United States Patent
Hill et al.

(10) Patent No.: US 10,984,528 B2
(45) Date of Patent: Apr. 20, 2021

(54) SYSTEM AND APPARATUS FOR CLINICAL DECISION OPTIMISATION

(71) Applicant: VOLPARA HEALTH TECHNOLOGIES LIMITED, Wellington (NZ)

(72) Inventors: Melissa Hill, Wellington (NZ); Ralph Highnam, Wellington (NZ); Julian Marshall, Los Altos, CA (US); Dave Murray, Tauranga (NZ); Lisa Renee Johnston, Wellington (NZ)

(73) Assignee: VOLPARA HEALTH TECHNOLOGIES LIMITED, Wellington (NZ)

( * ) Notice: Subject to any disclaimer, the term of this patent is extended or adjusted under 35 U.S.C. 154(b) by 57 days.

(21) Appl. No.: 16/319,246

(22) PCT Filed: Jul. 19, 2017

(86) PCT No.: PCT/IB2017/054382
§ 371 (c)(1),
(2) Date: Jan. 18, 2019

(87) PCT Pub. No.: WO2018/015911
PCT Pub. Date: Jan. 25, 2018

(65) Prior Publication Data
US 2019/0287241 A1    Sep. 19, 2019

(30) Foreign Application Priority Data

Jul. 19, 2016 (NZ) .......................................... 722316
Oct. 13, 2016 (NZ) .......................................... 725196
Oct. 18, 2016 (NZ) .......................................... 725385

(51) Int. Cl.
*G06T 7/00* (2017.01)
*G06T 7/73* (2017.01)
(Continued)

(52) U.S. Cl.
CPC ............ *G06T 7/0012* (2013.01); *A61B 6/469* (2013.01); *A61B 6/502* (2013.01); *A61B 6/5217* (2013.01);
(Continued)

(58) Field of Classification Search
CPC ....... G06T 7/0012; G06T 7/0014; G06T 7/75; G06T 2207/10116; G06T 2207/30068;
(Continued)

(56) References Cited

U.S. PATENT DOCUMENTS 7,142,633 B2 * 11/2006 Eberhard ................ A61B 6/482
378/62
9,865,067 B2 * 1/2018 Highnam .............. G06T 11/005
(Continued)

OTHER PUBLICATIONS

Image quality assessment in digital mammography: part II. NPWE as a validated alternative for contrast detail analysis (Year: 2011).*
(Continued)

*Primary Examiner* — Nizar N Sivji
(74) *Attorney, Agent, or Firm* — Holland & Hart LLP

(57) ABSTRACT

The present invention relates to a system and apparatus comprising automated analysis and feedback on soft tissue imaging quality, including analysis and feedback in real time and in conformance with key parameters and metrics which affect the quality of an image. The system is arranged to implement a method wherein method for providing a qualitative and/or quantitative assessment of an image including several steps. The steps include using an imaging apparatus to obtain at least one soft tissue image of a patient and at least one test object image; deriving a soft tissue image parameter and statistical data from image data from the soft tissue image. The system and method are characterised by employing a metric for the assessment in comparison to the parameter and statistical data, wherein the metric is obtained
(Continued)

from the soft tissue image data, data obtained from the at least one test object image, and data from the imaging apparatus.

19 Claims, 35 Drawing Sheets

(51) Int. Cl.
    *G16H 30/40*     (2018.01)
    *A61B 6/00*     (2006.01)
    *G16H 40/20*     (2018.01)

(52) U.S. Cl.
    CPC .......... *A61B 6/5282* (2013.01); *G06T 7/0014* (2013.01); *G06T 7/75* (2017.01); *G16H 30/40* (2018.01); *G06T 2207/10116* (2013.01); *G06T 2207/30068* (2013.01); *G06T 2207/30168* (2013.01); *G16H 40/20* (2018.01)

(58) Field of Classification Search
    CPC .......... G06T 2207/30168; G16H 30/40; G16H 40/20; A61B 6/469; A61B 6/502; A61B 6/5217; A61B 6/5282
    See application file for complete search history.

(56) References Cited

U.S. PATENT DOCUMENTS

| | | | | |
|---|---|---|---|---|
| 2004/0264628 | A1* | 12/2004 | Besson | A61B 6/4042 378/5 |
| 2006/0274145 | A1* | 12/2006 | Reiner | G06F 19/321 348/62 |
| 2006/0274245 | A1 | 12/2006 | Reiner | |
| 2007/0248210 | A1* | 10/2007 | Seise | G06T 7/73 378/37 |
| 2010/0086189 | A1 | 4/2010 | Wang et al. | |
| 2011/0216949 | A1* | 9/2011 | Yang | G06T 7/11 382/128 |
| 2012/0063567 | A1* | 3/2012 | Smith | A61B 34/30 378/37 |
| 2017/0202530 | A1* | 7/2017 | Mainprize | A61B 6/469 |
| 2018/0168531 | A1* | 6/2018 | Abdolell | G06K 9/6256 |
| 2019/0159741 | A1* | 5/2019 | Fredenberg | A61B 6/5235 |

OTHER PUBLICATIONS

Image Quality Ranking Method for Microscopy (Year: 2016).*
Figure of Image Quality and Information Capacity in Digital Mammography (Year: 2014).*
Anatomical background noise power spectrum in differential phase contrast breast images (Year: 2015).*
Analysis of biomedical spectra and images: from data to diagnosis (Year: 2000).*
Marshall NW: "A comparison between objective and subjective image quality measurements for a full field digital mammography system"; Physics in Medicine and Biology, Institute of Physics Publishing, Bristol GB, vol. 51, No. 10, May 21, 2006 (May 21, 2006), pp. 2441-2463.
PCT International Search Report for PCT International Patent Application No. PCT/IB2017/054382, dated Dec. 13, 2017.

* cited by examiner (Melissa 1)

(Melissa 2)

(Melissa 3)

(Melissa 4)

(Lisa 4)

(Lisa 5)

SYSTEM AND APPARATUS FOR CLINICAL DECISION OPTIMISATION

CROSS REFERENCE TO RELATED APPLICATION

This application is a U.S. National Entry and claims priority to PCT International Patent Application No. PCT/IB2017/054382, filed Jul. 19, 2017, and entitled "System and Apparatus for Clinical Decision Optimisation", which claims priority to New Zealand Patent Application No. 722316 filed Jul. 19, 2016, New Zealand Patent Application No. 725196 filed Oct. 13, 2016, and New Zealand Patent Application No. 725385 filed Oct. 18, 2016, the entire disclosures of which are incorporated herein by this reference.

FIELD OF THE INVENTION

The present invention relates to a system and apparatus comprising automated analysis and feedback on soft tissue imaging quality, including analysis and feedback in real time and in conformance with key parameters and metrics which affect the quality of an image. In particular it relates to system which adjusts the parameters via statistical counter-data to enhance interpretation of imaging physics data, anticipate error and suggest remedies.

BACKGROUND

Mammography is a specialised medical imaging procedure which uses low-dose x-ray to image the breast. Mammography has three main purposes: screening, diagnosis and intervention. Screening mammography entails imaging an asymptomatic population to detect breast cancers, ideally at an early stage; diagnostic mammography entails imaging for the purpose of diagnosing an abnormality discovered by physical exam or screening mammography; and intervention entails performing subcutaneous procedures under x-ray guidance.

For most women, screening mammography is performed on an outpatient basis and comprises a generally routine procedure whereby each breast is positioned between compression plates and an image receptor, the breast is compressed usually by a paddle to a preselected compression pressure, and images are taken from two angles—cranio-caudal (CC) and medio-lateral oblique (MLO). These steps are generally repeated for both breasts. In some women, body habitus will require the acquisition of additional images to ensure a complete exam that includes all breast tissue.

Furthermore, image quality is complex, with variability at each stage of an imaging chain of steps in a method for obtaining an image of soft tissue, and interplay between each element of the imaging chain; including physical characteristics of the imaging device, image acquisition technique factors, intrinsic subject characteristics, the skill of the operator, the effect of any processing applied to the image, the method of image display, and the psychometric factors involved in image visualization and interpretation for diagnostic decision-making.

The accuracy and therefore usefulness of each image depends on the correct positioning of the breast: the absence of any confounding materials such as other body parts; and adequate compression pressure. Compression of the breast is required in order to: immobilise the breast to avoid image unsharpness; flatten the breast to minimise tissue overlap for better visualization; minimize the thickness of tissue and thereby the amount of radiation required; and reduce x-ray scatter which may lead to degradation of image quality. The breast must not be over-compressed as it may cause discomfort to the subject. As soon as each image is acquired, the breast is released from compression. As a result, and because the C-arm of the mammography x-ray machine must be rotated to adequately position the patient for the next view, the breast must be manipulated and repositioned each time.

Optimally the resulting image has sufficient spatial resolution (detail) to image small structures (including micro-calcifications) and sufficient contrast to make soft tissue masses and other lesions evident.

A patient's anatomy affects positioning: the patient's height, size, weight and shape, patient breast size and shape, breast tissue composition, surface features and other artefacts, abnormal body habitus such as kyphosis, and the degree of discomfort felt and tolerated by each patient. Patient cooperation (for example, leaning in to the machine, remaining still and holding the breath as directed) is important for example to stabilize the patient and avoid image unsharpening due to patient motion.

Ascertaining the quality of an image and thereby which images are most appropriate for screening and diagnostic purposes, relies on the skill of the radiographic technologist, who visually assesses each image after it has been taken. In 'checking' the image, the radiographic technologist might assess whether the image meets internal, or local, regional or national standards and can be deemed 'acceptable'. If an image is not deemed 'acceptable' by the radiographic technologist, s/he may determine that it is necessary to acquire an additional replacement image or a variant of the original image. Once all necessary views have been acquired and 'accepted', the images are sent to the clinician for a screening or diagnostic reading. Preferably, in preparation for the reading, other prior mammographic images from the same patient are also sent to the clinical workstations for simultaneous review. The clinician will also benefit from having related images of the breasts from other diagnostic imaging studies, both current and prior, from modalities such as, but not limited to: ultrasound; magnetic resonance imaging (MRI); positron emission mammography (PEM); breast specific gamma imaging (BSGI); and contrast enhanced spectral mammography (CESM).

In 'reading' a collection of images the clinician can correlate physiological features such as general shape and size of the breast, the nipple, skin line and pectoral muscle and distances within; and 'match' features to establish concordance.

Even if the position of the breast appears optimal at image acquisition, many errors cannot be anticipated or overcome even with the skill and experience of a system operator or clinician, and images are routinely rejected and repeated because of unanticipated defects in imaging quality.

For screening and diagnostic purposes, other parameters are also considered, such as the tissue composition of the breast; glandular pattern; historical events such as history of prior benign or malignant disease, prior biopsies or surgeries, trauma, and other characteristics, for example artefacts such as clips, lesions, and matching features. Knowledge of other patient information at the time of mammography image reading may further inform the thresholds a clinician might use for detection of disease when 'reading' the mammogram and related images. One such ancillary piece of patient clinical information is the woman's propensity toward breast cancer, otherwise known as her risk of developing breast cancer.

PRIOR ART

A number of approaches exist which offer means both to estimate risk and guide either screening regularity or additional and adjunctive diagnostic screening: for example, the American Cancer Society guidelines on screening regularity by percentage propensity and the Tyrer-Cuzick (IBIS), Penn II, BOADICEA, and BRCAPRO models which include means to predict risk of pathogenic mutation and referral for genetic testing; and similarly, the Gail Model, which helps determine whether the patient may benefit from use of a medication to reduce her risk of developing breast cancer. None of the models include all known risk factors, and the estimated absolute risks can vary dramatically between models. Furthermore, a woman's individual risk factors change over time, as family propensity can become more evident, perhaps through announcement of a breast cancer detected in a close relation such as a sister.

A known, common limitation is that all models underestimate rates of breast cancer at the population level, and have varying degrees of accuracy at the individual level.

Breast tissue composition is a risk factor and an important inclusion in risk assessment models: for example, the proportion of the breast comprised of fibroglandular tissue, as opposed to fatty tissue. It is understood that the higher the density of the breast, implying a greater proportion of fibroglandular tissue, the greater the risk of developing breast cancer and or the greater the risk that cancers can be missed during screening—cancers can be masked by dense tissue. Dense tissue is also connected with a propensity to retake images due to poor positioning and low level of sharpness, which is more evident. Imaging systems which automate assessment of density are known (ref PCT/GB2010/001742 and tools such as Volpara® Density™). These are often integrated into risk models. Further, the relationship between fat and fibroglandular tissue is believed to be a factor in breast cancer risk and breast cancer development, assuming a parasitic relationship between cancer cells and support tissue around tumours.

The usefulness of all such factors relies on the quality of the image and optimised procedure, especially for 'dense' breasts (by which we mean breast with a high percentage of firbroglandular tissue) which are associated with high risk. However, there does not currently exist any commentary, guidance and corrective measures for the clinician during the imaging procedure to help achieve the optimal image.

Methods and systems exist for the consolidation and comparison of data in respect of query performance, however, there is a paucity of standards against which to compare consolidated data as data is non-standard: differing between the sites differs, measuring techniques and such problems are confounded by the sheer volume of data for comparison.

That is, there was no satisfactory means whereby a radiographic technologist was informed during the imaging session, immediately post-image or otherwise prior to a subsequent and further imaging procedure (referred to collectively as 'real-time') whether a patient's position during imaging would produce an image that meets the requisite standards.

Clinical image quality was usually assessed by applying objective quantitative metrics to images of test objects that are designed to represent average subject characteristics. Some basic test object tests were performed routinely to monitor system consistency, and other more complex tests were applied at specified intervals to benchmark system performance. These tests were applied to evaluate image quality achievable with modifications to a particular imaging system, to objectively compare the image quality between system types, and to ensure that minimum acceptable limits are being met in clinical practice. While practical to measure, the disadvantage of these simple image quality metrics was that they are independent of subject characteristics, skill of the operator (e.g. radiographic technologist) and were not directly suggestive of the ultimate diagnostic performance.

Image contrast and Contrast to Noise Ratio, CNR, were usually measured by physicists during routine image system testing using simple objects on a uniform background (e.g. 0.2 aluminium in Europe as per European Reference Organisation for Quality Assured Breast Screening and Diagnostic Services protocol and an acrylic disk/cavity, each against a 4.5 cm thick polymethyl methacrylate background in the USA. There was a known difference in material composition and thickness between the object and background.

While attempts have been made to make CNR measurement more efficient through automation, the process still relied on the use of images test objects for evaluation. Due to the requirement for known object and background compositions and thicknesses for consistent measurements, it was a difficult task to evaluate these types of quantities from clinical images with patient anatomy that varies in terms of size and composition.

Discussion in the prior art related to imaging quality metrics may be found in: (1) Metz and Vyborny, 1983; (2) Allec, Scott et. al., 2012; (3) Barrett et. al. 1995; (4) Zhou et. al., 2011; (5) Baldelli et. al. 2009, 2010; (6) Cederstrom and Fredenberg 2014; (7) Wang et. al. 2014; (8) Samei et. al, 1998; (9) Hogg et al 2012; (10) Kinear and Mercer, 2016; (11) Christianson et al 2015; (12) Chun et al 2015; (13) Tian and Samei, 2016; (14) Karssemeijer et. al. 2005; (15) Marshall et. al. 2011; (16) Revesz 1985; (17) Pakdel et. al., 2014; (18) Sanders et et. al., 2016; (19) Allec et. al., 2012; (20) Hill et. al., 2013; (21) Allec, Lewin et. al., 2012; (22) Hill, Muller et al 2013; (23) Hill, Saab-Puong et. al., 2013; (24) Ma et al 2015; (25) van Engen, Young et. al., 2006; (26) Saunders et. al. 2007; (27) Brammer, Bullmore et. al., 1998; (28) Artman, 2016, Ma et. al. 2015.

SUMMARY OF THE INVENTION

According to a first aspect of the invention there is a method for providing a qualitative and/or quantitative assessment of an image including the steps of: using an imaging apparatus to obtain at least one soft tissue image of a patient; deriving a soft tissue image parameter and statistical data from image data from the soft tissue image; characterised by employing a metric for the assessment in comparison to the parameter and statistical data, wherein the metric is obtained from the soft tissue image data, and data from the imaging apparatus.

According to a second aspect of the invention there is a method for providing a qualitative and/or quantitative assessment of an image including the steps of: using an imaging apparatus to obtain at least one soft tissue image of a patient and at least one test object image; deriving a soft tissue image parameter and statistical data from image data from the soft tissue image; characterised by employing a metric for the assessment in comparison to the parameter and statistical data, wherein the metric is obtained from the soft tissue image data, data obtained from the at least one test object image, and data from the imaging apparatus.

Preferably the parameter is derived for a region of the soft tissue image.

Preferably statistical data relating to a noise and/or contrast signal is derived for a region of interest (ROI) in the soft tissue image.

Preferably deriving the statistical data includes deriving an image power spectra characterization in the ROI.

Preferably an account is taken of the image power spectra characterisation that is influenced by noise from the apparatus.

Preferably a statistical account is taken of the image power spectra characterisation that is influenced by noise from an anatomical structures in the soft tissue.

Preferably the statistical data is derived for sharpness of an image in the ROI.

Preferably the method includes the step of determining whether the sharpness of an image is below a preselected level attributable to motion of the soft tissue while obtaining the image(s).

Preferably the method includes determining sharpness below a preselected level in or proximate an anatomical artefact in the tissue.

Preferably the method includes determining sharpness below a preselected level attributable to motion of the anatomical artefact in the soft tissue while obtaining the image(s).

Preferably the method includes identifying location(s) where in a first one of the images the image sharpness is below a preselected level by determining where in the first one of the images the image power spectra is within a preselected criteria.

Preferably the method includes determining the density of the tissue as the parameter and identifying where in the first one of the images there is overlap of the location(s) where the sharpness is below the preselected level and location(s) where the density is above a preselected criteria.

Preferably the parameter derived includes thickness, composition, or density of a compressed breast included in the soft tissue in the image.

Preferably the method includes determining whether regions of interest (ROI) within a constant thickness region within the tissue overlap on the image.

Preferably the contrast is computed from the image intensity of pixels at locations where the density is relatively high and low.

Preferably the imaging quality metrics include positioning metrics derived from the location and orientation the soft tissue in the images.

Preferably the method includes characterising the image (s) by scores derived the data, parameters, and metrics.

Preferably the method includes classifying the scores according to information of the imaging apparatus, clinic where the image is acquired, or clinician who obtained the images.

Preferably the method includes deriving an Overall Quality score from a plurality of the scores.

Preferably the method includes deriving an Overall Productivity score from a plurality of the scores.

Preferably the method includes deriving an overall Effectiveness score the overall Quality score and overall productivity score.

Preferably the method includes reading of compression force recorded while obtaining the image(s) and an analysis of the image(s) deriving a target force for applying a target compression pressure to be applied to the soft tissue of the patient by the apparatus for obtaining a next image and including the target force in the feedback.

According to a third aspect of the invention there is a system for operating as means for implementing the method described herein. Preferably the system includes means for uploading and downloading data for analysis from and to the Cloud.

Automated Analysis

The present invention provides a system and apparatus for automated analysis and feedback on imaging quality, including analysis and feedback in real time and in conformance with key parameters and metrics which affect the quality of an image.

It is an advantage of the invention that images may be used within means to adjust parameters of image analysis.

Further, the present invention consolidates data, compares data and uses statistic counter-data to enhance interpretation of imaging physics data, anticipate error and present remedies.

The system and apparatus provide for real-time verification of the accuracy and quality of an imaging procedure. Images are captured and optionally stored, including images otherwise previously rejected, for use as statistical counter-data to enhance interpretation of the imaging physics data, anticipate error and present remedies, including providing additional training to radiographers who may be struggling in some aspects of patient positioning, and provide managerial oversight of technologist performance. The system further records and presents guidance on imaging parameters e.g. force, physiological features, patient context and historical treatment criteria, error appraisal, pre-acceptance and post-acceptance prompt (e.g. reject, repeat vis-à-vis individual); reason and resolution of basis for rejection.

In an embodiment diverse image quality parameters are available on selection to help interpret any bias or other considerations in the image analysis.

In an embodiment, each image is evaluated for quality as soon as it is acquired. For example, a quality-check software algorithm might first evaluate the image quality for the most recently acquired image, and then secondarily perform additional quality checks on that latest image in comparison to any previously acquired images in the current study, prior studies, or prior studies from other modalities. As more images are acquired in the course of the study, the opportunities to further inform, cross-checking with other images, increases. Alternatively, the image quality checks may not occur until all of the images have been acquired and the images have been quality-checked at the close of study.

In an embodiment, the x-ray system sends all the images before individual image 'acceptance' by the radiographic technologist to a quality-checking software module or application, or to a device such as a tablet or server running a quality-checking software application, to provide feedback on image quality under time restraints. The x-ray system sends each image deemed 'acceptable' by the radiographic technologist, perhaps after the time-restrained quality feedback is received, to 'after acceptance' analysis, which entails a lengthier and more complex quality-check, and may be performed either in faster on-premises computers or via the Cloud, with results delivered back to the radiographic technologist.

Image Quality Metrics

Conspicuity (meaning how well a given feature stands out from surrounding structures) is influenced by three main image properties: contrast, noise and sharpness.

Contrast

Contrast is the most basic conspicuity descriptor, and is usually defined in terms of the difference in image intensity between an object of interest and the background. A simple version of contrast (C) can be defined in terms of image signal difference.

Contrast is the absolute value of the difference between the mean image intensity in a region of an image of an object of interest and the mean image intensity in a background region of the image. The background region is region in image where there is no tissue. In mathematical terms, contrast is defined by Equation 1 as follows:

$$C = |\langle ROI_{obj}\rangle - \langle ROI_{obj}\rangle|$$

where $ROI_{obj}$ and $ROI_{bkgnd}$ represent intensities at pixel locations in object and background regions of interest (ROI), respectively. The angled brackets denote calculation of mean image intensity over the ROI, and the absolute value ensures that contrast is always calculated as a positive value. Preferably the system operates on a digital representation of the image. The contrast is determined from the intensity of all the pixels in the region of interest and all the pixels in the background.

The digital representation of the image includes pixels arranged in a two-dimensional grid. The pixels overlap or the edges of the pixels are touch so that the whole of the image is covered by the pixels. Digital images comprise a grid of adjacent pixels.

Each pixel comprises coordinates which locate it on the grid, and intensity associated with the density and thickness of tissue at the location in the image. In some embodiments of a digital representation of an image, further information is associated with each pixel.

In a digital image the region of interest, ROI, is within a portion of the grid. The grid is preferably defined by orthogonal coordinates in X and Y directions. Each pixel in the grid is located by coordinates $x_i$ and $y_i$. The size of the ROI is n×m image pixel lengths or diameters.

Noise

Noise in a radiographic image refers to the variations in image intensity caused by sources other than the patient anatomy. Image noise reduces the image apparent contrast and image sharpness, and therefore, conspicuity.

The simplest descriptor of image noise is the variance ($\sigma^2$) of the image intensity in a region of interest, ROI.

The image noise relevant to clinical imaging performance and analysis in a region of interest is defined by the variance of the intensity in the region of interest. The image noise is defined by a quotient of a numerator and denominator. The numerator is defined the sum of the squares of the difference between the intensity of the image the location of each pixel in the region of interest and the mean intensity of the image in the region of interest. The denominator is defined by the number minus one of pixel lengths which define the size of the ROI.

In mathematical terms, image noise in the region of interest as defined by the variance of the image intensity in the region of interest is defined by Equation 2 as follows:

$$\sigma^2 = \frac{1}{n-1}\frac{1}{m-1}\sum_{i=1}^{n}\sum_{j=1}^{m}[ROI(x_i, y_j) - \langle ROI_{obj}\rangle]^2.$$

Noise reduction in the image as a whole, and wherein the image of the soft tissue is located, wherein the region of interest is located, and the background has a major influence on improving clinical imaging performance. However, when noise reduction is achieved by increased radiation to obtain the image, the improvement in clinical imaging performance may be out-weighed by increased danger of the increased radiation dose in radiographic imaging. The principle of As Low As Reasonably Achievable (ALARA) radiation dose must be followed. Previous methods for measurement of noise in patient images have relied on the identification of homogeneous regions of interest (ROI), or the creation of homogeneous regions by subtraction of paired or sequential images. While useful for CT imaging where reasonably uniform image regions are available due to low contrast between soft-tissues, these approaches are not applicable to other imaging modalities such as mammography with high soft-tissue contrast.

Techniques for noise evaluation from patient images in mammography have focused on estimation of the quantum noise component. The present invention provides a novel method to estimate noise from patient images that overcomes some of the difficulties encountered when assessing soft-tissue images such as mammograms while estimating the entire image NPS rather than just the high frequency component. According to the present method, an estimate of the total image variance (e.g., Equation 2) can be made from a patient image that is an approximation to the noise that would be present if the image had a uniform appearance (like an image of a test object), but with the patient-specific effects of thickness, tissue composition, and soft tissue density on noise taken into account.

Sharpness

Image sharpness refers to the amount of true feature detail that can be reproduced in the image, and determines the smallest object that may be reliably detected. Sharpness is commonly evaluated in terms of the image point spread function (PSF), and/or the modulation transfer function (MTF), which expresses the system transfer of signal at each spatial frequency.

This approach would tend to underestimate the noise in an otherwise uniform image, because it ignores important contributions at lower frequencies evident in system NPS evaluations.

In radiography, lack of sharpness in an image can result from several factors, including the size and shape of the x-ray tube focal spot, signal spread in the image receptor, and patient motion.

Typical physics measurements of system MTF use static and uniform objects that may not adequately characterise clinical image sharpness, especially in the case of patient motion, which reduces the level of sharpness of the images and reduces clinical imaging performance.

For example, motion in mammography is relatively common, and the motion reduces the sharpness of mammographic images. Up to 20% of screening mammograms exhibit some elements of reduction sharpness due to motion of the patient while the image is obtained. The loss of sharpness is often not identified at the time of screening and therefore leads to patient recalls for image retakes: indeed, instances have been recorded where over half of technical recalls have been attributed to loss of sharpness.

Image sharpness estimates had been made from patient CT images by measuring the PSF and MTF at the air-skin interface. This approach relied on having a high contrast region consistently available in the image for sharpness measurement. Therefore, these sharpness estimation methods were not applicable in soft tissue images, especially those without a sharp skin-air boundary such as mammograms where the breast thickness reduces towards the skin line.

To address instances where there is an absence of structures in the image appropriate for MTF measurement, the present method uses the eNPS to evaluate image sharpness.

It is thus a further advantage that the above refines the imaging context. Regions of high density are identified, it is indicated whether a region of high density is sharp, or has a level of sharpness below a threshold (thereby alerting the radiographic technologist to the fact that the low level sharpness is more likely to mask a significant (i.e. cancerous) feature or that masking is in a region most prone to cancer).

Further the present invention uses a system such as that described in PCT/GB2010/001742 and via quantitative analysis of breast x-rays, to compare corresponding regions in more than one image, as described in PCT/GB2011/001658. For example, matching between CC and MLO correlate information in the CC and MLO views, modelling the geometric changes and using breast density to set the search boundaries around which the automated system looks for a matching object in the other view.

In an embodiment the present invention detects a matching or comparable 'focal density' (the term 'focal density' is used here to mean an area in a mammogram which demonstrates raised x-ray attenuation as compared to its background, and therefore indicate a volume of interesting tissue in the breast such as a potential cancer) in more than one image and provides a standardised display, such as a 'density map' for the images in a study, whereby the images or a feature in the images can be compared. As one option the display emulates a standard display of density in order to correlate historic images. The display might also display key features of each density map, for example, the density of the densest pixel, the density of the densest volume of tissue above any 1 cm2 region, and the overall breast density. In a preferred embodiment when there is a suspect region of high density, present and matching in both views of the breast (CC/MLO), then the density map shows the images in a standardized manner for comparison.

The present system and method are advantageous because they provide an efficient and patient-specific image sharpness that has the potential to decrease such recalls, with important socio-economic benefits.

Image noise relevant to clinical imaging performance and analysis in a region of interest is defined by the variance of the intensity in the region of interest. For digital images, the image noise may be calculated from Equation 2 above.

Image noise calculated by Equation 2 is only fully accurate when there is no correlation between intensities of adjacent pixels, such as for white noise. However, in practical imaging systems there are sources of that contribute to loss of sharpness and that create correlations between the adjacent pixel intensities. These correlated noise sources of loss of sharpness include x-ray re-absorption and patient motion.

The image autocorrelation function of an image signal describes correlated noise. The image autocorrelation function is commonly evaluated in the spatial frequency domain using the Fourier transform to map image signals from the spatial domain to the spatial frequency domain.

When initially obtained, image signal values are not necessarily linearly related to image intensity or the tissue density or tissue thickness through which x-rays penetrated before they were detected by a sensor that generated the image signals. Before linearization, a digital image signal comprises values of intensity, at each pixel location in a region of interest, ROI. The signal is then 'linearized' by a function which calculates linearized values of the intensity, I, corresponding to each nonlinearized value, ROI.

A first Noise Power Spectrum (NPS), is defined as the Fourier transform (F) of the image autocorrelation function, and gives the signal variance at each spatial frequency, $f_x$, and $f_y$. It can be computed from linearised image intensity, I, as follows from Equation 3.

$$\text{First NPS}(f_x, f_y) = |F\{I(x,y) - \langle I \rangle\}|^2$$

The first NPS is determined from the mean value of the linearised image, I. The angled brackets denote calculation of mean image intensity over the ROI at each pixel location, (x, y). The mean value of the linearised image intensity, I, is subtracted from the image at each pixel location, (x, y).

In practice, the mean value of the linearized image intensity is averaged over an ensemble of image realisations, or ROI from a single image, to meet a mathematical requirement that the data mean and covariance be position-independent on average.

The first NPS as defined by Equation 3 only accounts for imaging system noise sources (e.g., quantum, electronic, structured), and so care must be taken to remove signal-related image intensity variations such as from the heel effect.

A second NPS is specified by an IEC (2003) standard that accounts for signal related image intensity variations such as heel effect. Equation 4 below may be used to calculate the second NPS.

$$\text{Second } NPS(f_x, f_y) = \frac{p_x p_y}{mn} \langle |F\{I(x_i, y_j) - S(x_i, y_j)\}|^2 \rangle.$$

In Equation 4 to calculate the second NPS, S is a two-dimensional polynomial fit to the image. The length of the ROI in the x and y directions is defined by the number of pixels m and n in the x and y dimensions respectively, and the pixel size $p_x$ andy $p_x$ in the x and y dimensions respectively. The angled brackets indicate an ensemble average over all ROI.

Integration of Equation 4 for the second NPS over radial frequencies $f_x$ and $f_y$ from zero to the maximum sampled frequency gives the noise variance for the region under analysis, equal to that from Equation 2.

The radial frequencies are spatial frequencies, which means that the units of frequency are reciprocal of distance, typically 1/mm as the units. Radial frequencies are the spatial frequencies in a radial coordinate system, as opposed to the usual Cartesian coordinate system.

While normal anatomy provides an important reference for diagnosis in medical images, its appearance in an image is sometimes also considered to be a source of structured noise since it can mask the detection of a pathology. Thus, the NPS has been generalized to account for signal variations from the appearance of normal anatomy, or 'anatomical noise'.

In order to differentiate between noise sources included in the measurement by a sensor which provide the image signal, two different designations are used: NPS and eNPS.

Power spectra that only include system noise will be indicated by the NPS

Power spectra characterizations that include system and anatomical noise will be referred to as effective NPS (eNPS).

Although the NPS is strictly a measure of image noise, the eNPS includes signal from anatomical structures.

The present system and method are novel and advantageous by measuring the eNPS including motion which cause loss of sharpness during a single image acquisition The present system and method are novel and advantageous by analysis of the eNPS to detect and provide a quantitative indication of motion caused low levels of sharpness. The detection of motion caused loss of sharpness using the eNPS is a feature of the present invention.

Further, the present invention is novel and advantageous since it takes into the analysis that anatomy in the images which is difficult to analyze due a low level of sharpness will present a different eNPS to sharp images of the anatomy. The difference in eNPS is due to image intensity correlations introduced by motion when the same anatomical feature is imaged at more than one pixel location during a single image acquisition.

It is a particular advantage of the present method that it utilises simple image quality metrics derived from images of test objects and the observed clinical image quality that ultimately determines true diagnostic performance. Thus among other quality measures, a threshold is set for image 'sharpness', and metrics such as contrast, noise, and sharpness are used.

Compared to the exclusive evaluation of images of test objects, the present method is patient-specific and assesses the particular realization of image quality in the clinical image of interest: the effect of an individual's anatomy is minimized to address the image quality and reduce the impact of both the operator performance and the imaging system physical characteristics. Thus, the present method is also efficient compared to traditional methods in that the acquisition or assessment of separate reference images of test objects is not required, and as-such the present invention provides real-time monitoring of system physical characteristics that could indicate equipment malfunction or degradation, and that can also be used to identify operator—and/or patient-related deficiencies that may indicate the need for repeated imaging to achieve diagnostic quality.

Contrast to Noise Ratio

An important metric to describe the conspicuity of a given contrast relative to the image noise within which the contrast is to be detected is the contrast-to-noise ratio (CNR). The CNR can be calculated from Equation 5 as follows, $$CNR = \frac{|\langle ROI_{obj} \rangle - \langle ROI_{bkgnd} \rangle|}{\sqrt{(\sigma^2_{obj} + \sigma^2_{bkgnd})/2}}.$$

Radiographic system optimisation is often performed using a ratio of the CNR to the square-root of radiation dose as a figure-of-merit, thus, balancing the trade-off between improved image quality and increased radiation dose. For consistent and practical CNR measurements, these evaluations are made using simple images of test objects. However, patient-specific factors not captured by a uniform test object can influence the optimal technique factors for imaging.

An advantage of the present invention is the system determines contrast, noise and CNR in a patient-specific manner for a more accurate image quality assessment.

It is thus a feature of the present invention that it uses contrast and CNR measurements directly from patient images using breast composition data and thickness information to guide selection of image intensities for analysis. Such measures are objective and allow for direct comparison of contrast and CNR between images of different patients and between image acquired using different imaging systems.

Quality 'Score'

Scoring the Imaging quality metrics and positioning, along side tissue composition (e.g. density), determines, either through automated thresholding or user decision making, whether any retakes are necessary. In addition to an imaging quality score, a score can be attributed to the imaging environment. For example, the 'Overall Quality' and 'Overall Effectiveness' as well as attributes such socio-economic and demographic indicators, many of which are recognised as complementary indicators of propensity towards cancer.

In an embodiment imaging data is automatically extended to the Cloud for analysis and the automatic removal and subsequent re-application of protected health information (PHI) to anonymized data in the Cloud.

In an embodiment the present invention provides improved means to combine various data points for breast imaging centres to get to 'Overall Quality' and 'Overall Effectiveness' scores.

The Overall Quality score is shown versus Overall Productivity score to demonstrate Overall Effectiveness, for example, the effectiveness of a breast imaging centre. These scores are compared between sites for example to ascertain which centre or centres is optimizing productivity without compromising quality. The scores can also be compared within an organisation and/or to unaffiliated institutions, regional, state or national metrics to see how one Enterprise compares to another. Additionally, the Overall Effectiveness and Overall Productivity can be mapped or otherwise graphically displayed.

Preferably the patient-specific image quality metrics and scores are integrated within an overall quality system for comparing imaging apparatus, teams, and clinics. Preferably the overall quality system provides graphical representation of 'Overall Quality v Overall Productivity'.

When the imaging data is received from different imaging apparatus and modalities, the data is standardized, for example, a standard radiation dose measurement algorithm is applied. Similarly, a standardized compression measurement is applied which might, for example, prioritise compression pressure in preference to force. Obtained cancer detection rate and other clinical parameters might be achieved via integration and data collection from other electronic systems.

Preferably prior image data in the Cloud is scheduled and re-processed via newly deployed algorithms, thus the amount of useful data available per image is extended and additional data values are extracted from new studies acquired using the new image analysis algorithms. To illustrate, Cloud-based medical image analysis and data quality systems receive and analyse images from acquisition modalities. During the process meta data is extracted from the image headers, along with some form of pixel data from the images, and is sent to the Cloud for storage and ongoing comparisons, trending and charting.

According to the present invention, prior image data in the Cloud is scheduled and processed via newly deployed algorithms and empty data points populated in an expanded data table. Thus new factors become available for all prior images making data analysis over time on the new factors possible. The processing can be accomplished either by: retrieving the pixel data from the Cloud to the system, processing the pixel data preferably in the system, then returning the new data values to the Cloud to populate the existing table rows.

Also preferably, pixel data received from the Cloud to the system is returned to the could with instructions for performing the processing in the Cloud.

Preferably an analogous approach is used to replace existing data fields in the Cloud should an updated (replacement) algorithm became available and data replacement a desired outcome.

Many breast imaging centres do not store raw data from mammograms on the premises. Providing significant new data, evaluated temporally, via a process whereby raw data is retrieved from historic cases from the Cloud, sent back to the facility, re-identified, re-processed and the new results based on the historic data are sent back to the Cloud. Thus, temporal comparison becomes available shortly after deployment of a new algorithm.

To meet the security requirements, PHI databases in the Cloud are stripped of most of identifying materials. Comparison of machine and operator performance data is not effected. However, a site may want to look at the actual patient images, in which case secure means to re-identifying the patient is required. Two preferred methods are: 1) to replace the data with a hash code that cannot be decoded at all, perhaps with a reverse look-up table being retained in the originating clinical site; or 2) to anonymize the data by removing any patient identifying attributes altogether.

In one embodiment of the present invention, patient data is placed into the Cloud according to 1) whereby, the hash coding method is used to produce replacement values that, once in the Cloud, show for Patient Name, Patient ID and Patient Date of Birth (DOB). To enable traceability back to the patient, a look-up table containing the mapping is stored and secured on-premises rather than in the Cloud. The data can be retrieved from the Cloud by applications for data mining the data stored there. If the retrieving application is outside the related health care provider network, and not tunnelling into the network via a Virtual Private Network (VPN) or other secure connection (as below), the hashed data is not able to be decoded.

The same applies within the Cloud (or from outside via VPN connection). The data is still hashed when viewed. However, it is a further advantage of the present invention that by means of an additional step by the web browser (or other authorized tool accessing the Cloud data) there is provided a reverse look-up of the hash value in the on-premises table of hashed values, allowing the original data to be revealed to the authorized users.

Once the radiographic technologist is satisfied with the quality of each individual image based on her/his observation of the images and the 'before acceptance' and/or 'after acceptance' scores, the radiographic technologist indicates 'close of study', which indicates that there is no intention of taking additional images—the patient is dismissed at this time. In one embodiment the images may then be sent to a 'close of study' image quality checking software module for complete analysis, perhaps with more complicated algorithms that take into consideration the correlation of positioning date between contralateral and orthogonal views of the breasts and produces a 'study score' assessment of quality for the study.

The invention will now be described, by way of example only, with reference to the accompanying drawings in which:

BRIEF DESCRIPTION OF THE FIGURES

FIG. 5 illustrates an exemplary method of noise estimation from a digital mammogram by a novel NPS estimation from the image eNPS comprising:

FIG. 6 illustrates an exemplary embodiment of clinical image contrast measurement comprising:

FIG. 7 illustrates a typical presentation of motion caused low level of sharpness in mammography, and demonstrates an exemplary embodiment of level of sharpness detection comprising:

FIG. 17 shows the medial and lateral nipple direction, wherein;

DETAILED DESCRIPTION OF THE INVENTION

Figure 1:
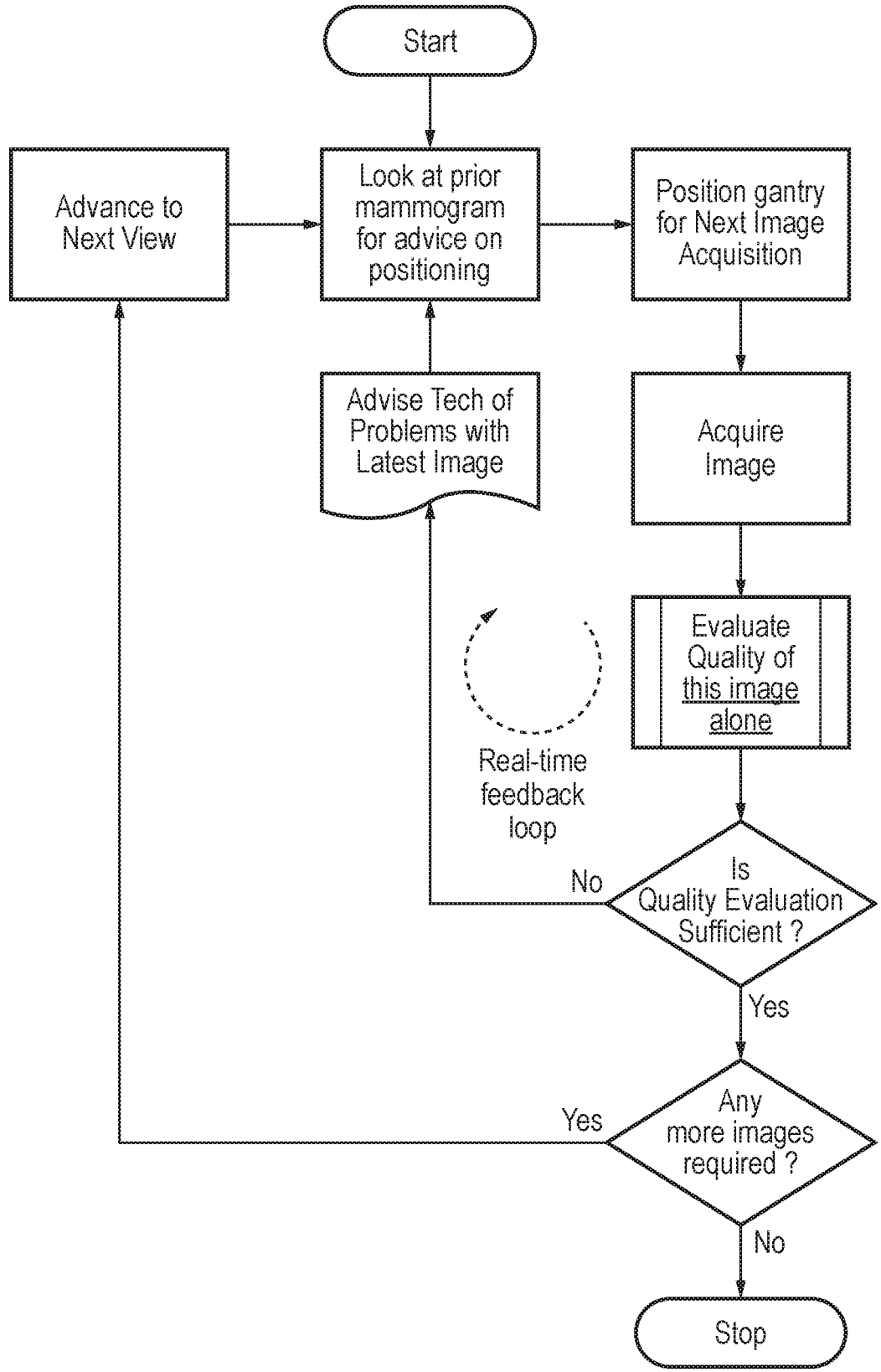
FIG. 1. shows an image quality real-time check based on checking the most recent image.
Figure 2:
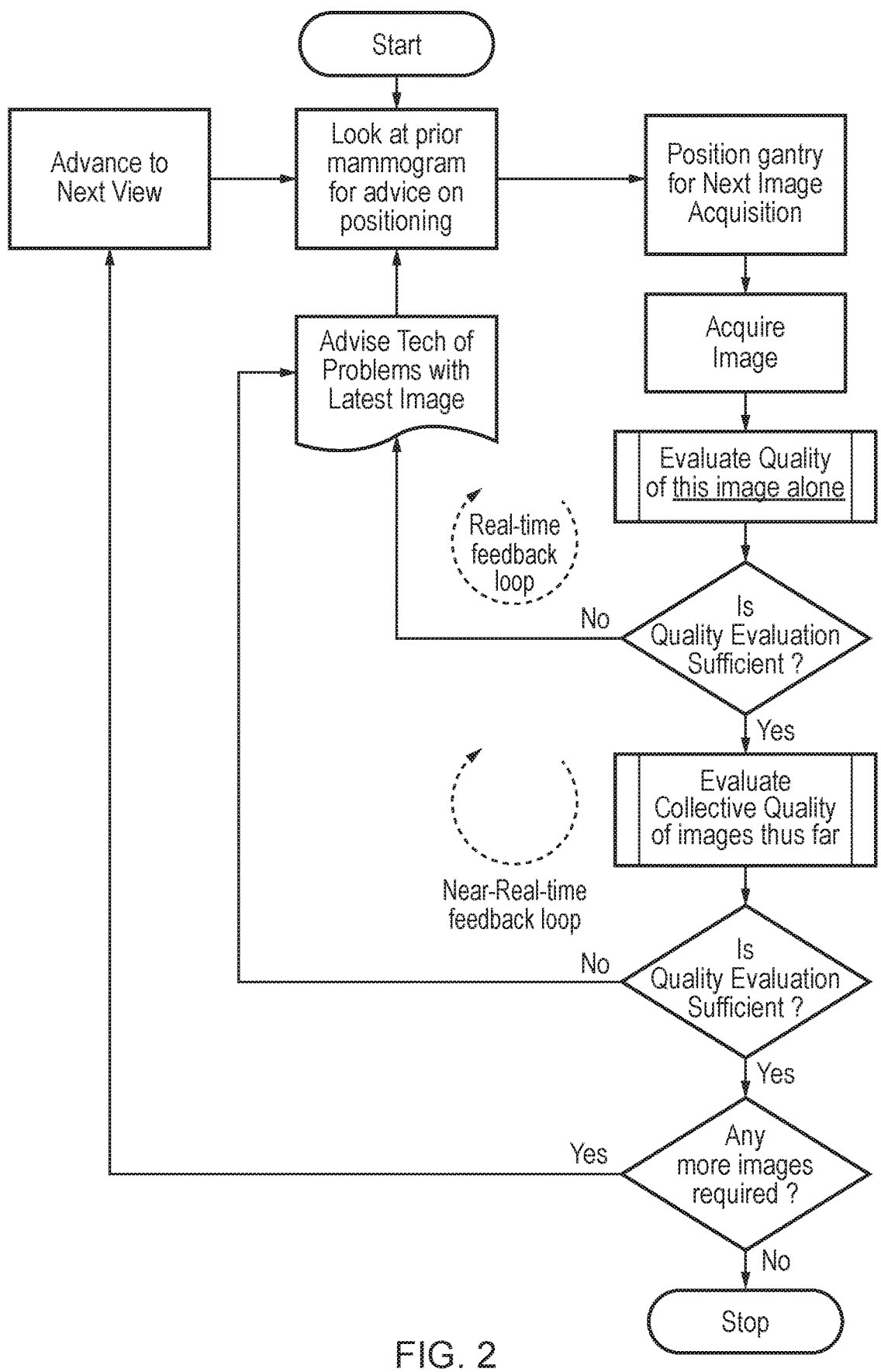
FIG. 2. shows an image quality check based on both the most recent image and on previous collected images.

In an embodiment, a radiographic technologist logs in using a confidential log-in for example via user name and password, biometric identification or other.

The patient is identified via electronic communication of patient context from the mammography x-ray system or by reception of the first image from the scanner which contains patient demographic information in the DICOM header, through selection of the patient from a patient worklist or through manual entry of Patient name, MRN, and the date of the study. A software module retrieves the prior screening mammogram of the identified patient from PACS and performs an analysis on each view that computes the area of the breast in the image. From the Compression Force recorded at the time the image was acquired, the software computes the Compression Pressure that was applied at the time. An analysis is then performed to predict the amount of Compression Force that should be applied to that patient during the present screening using the present apparatus to reach a target Compression Pressure, such as 10 kPa.

To elaborate, by way of example: i. an area of a portion of a paddle which compressed the breast is estimated from at least one previous mammogram; ii. a compression pressure used is calculated, taking the force used from the DICOM header and dividing it by the area estimated in i. (it is assumed that the area will not change for the present procedure); iii. an estimated force is calculated that will apply a specified pressure, for example, 10 kPa pressure or other appropriate target pressure is for the facility. Where there is no a priori estimation, the contact area from the first image might be used to estimate force for a subsequent image and/or indicate the need to retake the initial image.

Some adjustment can be made if the body habitus has changed significantly for the patient in the period between procedures. Where additional data, including risk data, is available, the above is adjusted accordingly: for example, if weight or body mass index (BMI) data is available and the patient has changed weight or body mass, more or less force should be applied.

A scale factor may be used to adjust the influence of body habitus change on Compression Force.

The software then displays to the Radiographic Technologist a target Compression Force for each of the mammographic views that are to be acquired.

The radiographic technologist then positions the patient for each view that is to be acquired, applying Compression Force similar to that recommended by the software, which will approximate the target Compression Pressure of, for instance, 10 kPa.

Once the images have been acquired the actual Compression Pressure can be calculated. Evaluating the difference between the applied Compression Pressures and the target Compression Pressure may indicate the need to adjust the scale factors.

In a further step, quality criteria are appraised relating to the patient position. For example, in FIG. 1, steps of a method are illustrated for evaluation of image quality by quality criteria.

Density score—In one embodiment, a density of a breast in an image i is computed as a metric via an automatic density measure such as that described in PCT/GB2010/001472 page 14 lines 20 to 25, page 16 lines 4 to 9, and page 18 lines 23 to 26; or using tools such as Volpara® Density (trade mark) along with positioning metrics. A density score is displayed in letter form (for example, A, B etc), numerical form (for example, 1, 2 etc or a percentage), or graphical form, (for example a map where the density of a breast is computed from CC and MLO images and mapped in 3D).

A metric for the position of the breast in the image may also be calculated.

Figure 10:
FIG. 10. shows the inframammary fold.

Positioning metrics may be displayed individually (i.e. nipple not in profile) or as proportions of images (i.e. what percentage of images have nipple in profile). Nipple in profile and Inframammary Fold (i.e. IMF) metrics may be displayed individually and may be presented as proportions of images where the nipple is in profile and IMF is visible respectively. The inframammary fold, IMF, shown for example in FIG. 10.

Metrics may also be displayed in statistical form, for example the average pectoral angle. Further metrics can be incorporated into a positioning score per image and per study. For example, in one embodiment the metric(s) and the algorithm(s) are used to derive the overall positioning score for position of the breast in the image. These metrics comprise the following:

Nipple in Profile—the Nipple in Profile is computed for both the MLO and CC views. The nipple location is detected and the nipple area is defined. In a preferred embodiment the nipple is considered to be in profile if at least 5%-15% of the nipple area is anterior to the skin boundary of the breast.

Inframammary Fold Visible, (IMF)—the inframammary fold is detected by identifying a corner in the inframammary region and computing the area of that region. A threshold is then applied by which the minimum area will be accepted as the IMF being visible.

Figure 11:
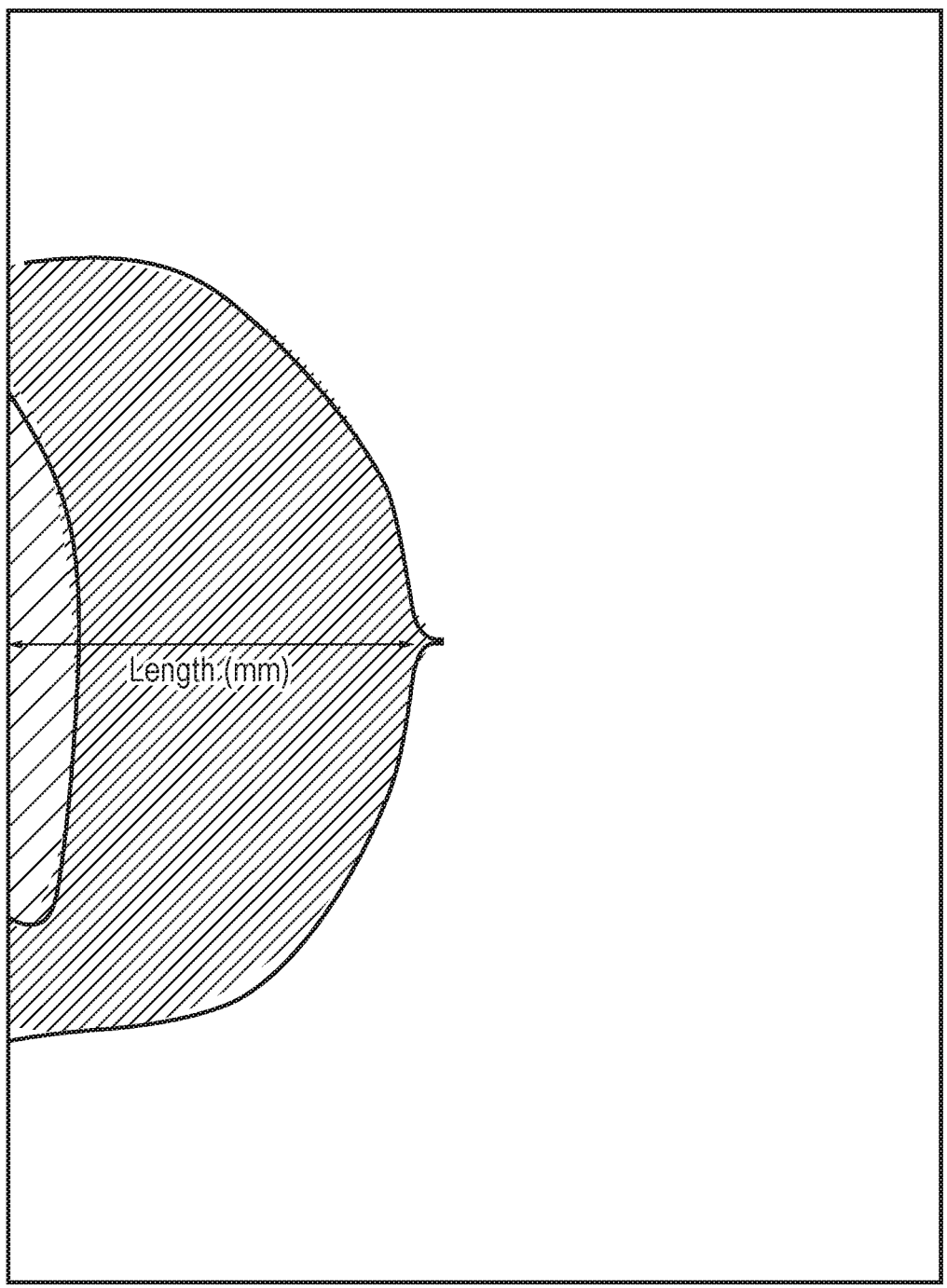
FIG. 11 shows the posterior nipple line length on an image of a CC view.

Posterior Nipple Line, (PNL) length—the posterior nipple line (PNL) is shown in FIG. 11 and FIG. 12. The PNL length is computed for the MLO and CC view.

For the CC view shown in FIG. 11 the nipple is located and a line, for example a horizontal line, that is substantially normal to the chest wall, is measured from the nipple/skin boundary to the posterior edge of the image. The length of the line measured in the PNL length.

Figure 12A:
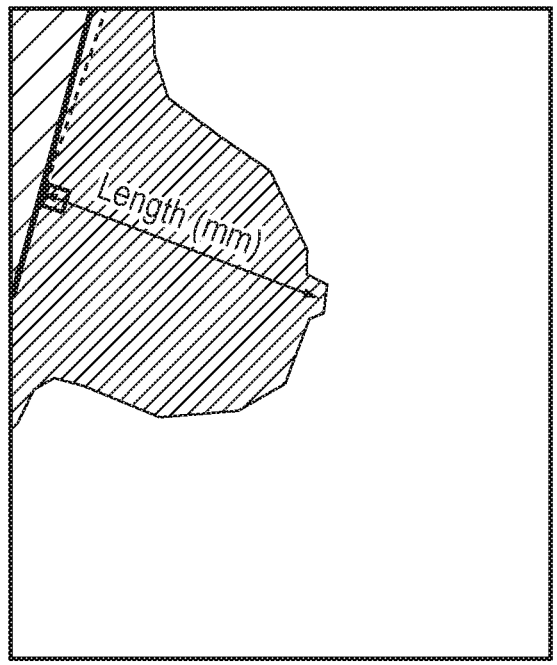
FIG. 12 shows the posterior nipple line length on an image of an MLO view where the posterior nipple line intersects the anterior margin of the pectoral muscle (FIG. 12A) or the posterior image edge (FIG. 12B)
Figure 12B:
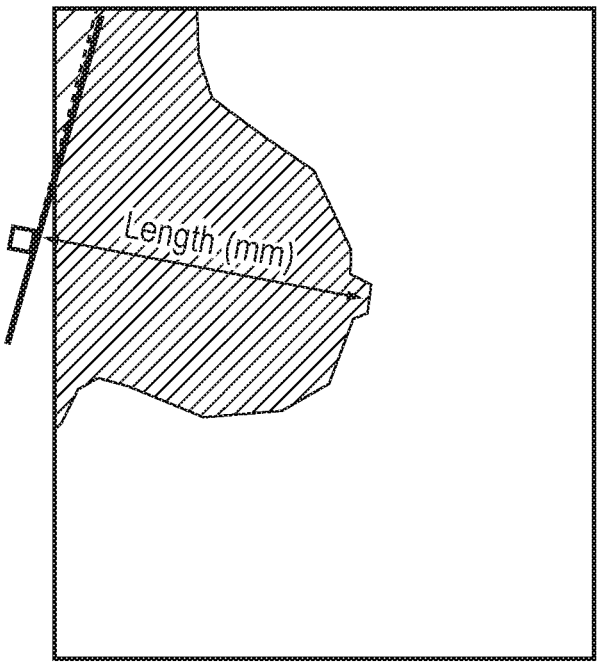

For the MLO view the PNL length is measured along a line from the nipple/skin boundary to the anterior margin of the pectoral muscle or the posterior image edge (whichever comes first). This line is drawn at an angle to the pectoral muscle, for example a 90-degree angle to the pectoral muscle as can be seen in FIG. 12A, or an extended straight line estimate of the anterior edge as can be seen in FIG. 12B. The PNL line length differs from the compressed thickness and density which are computed with respect to thickness of dense tissue hint as described in publication A1 of PCT/GB2010/001472, page 8, line 17 to page 9 line 1.

Figure 13:
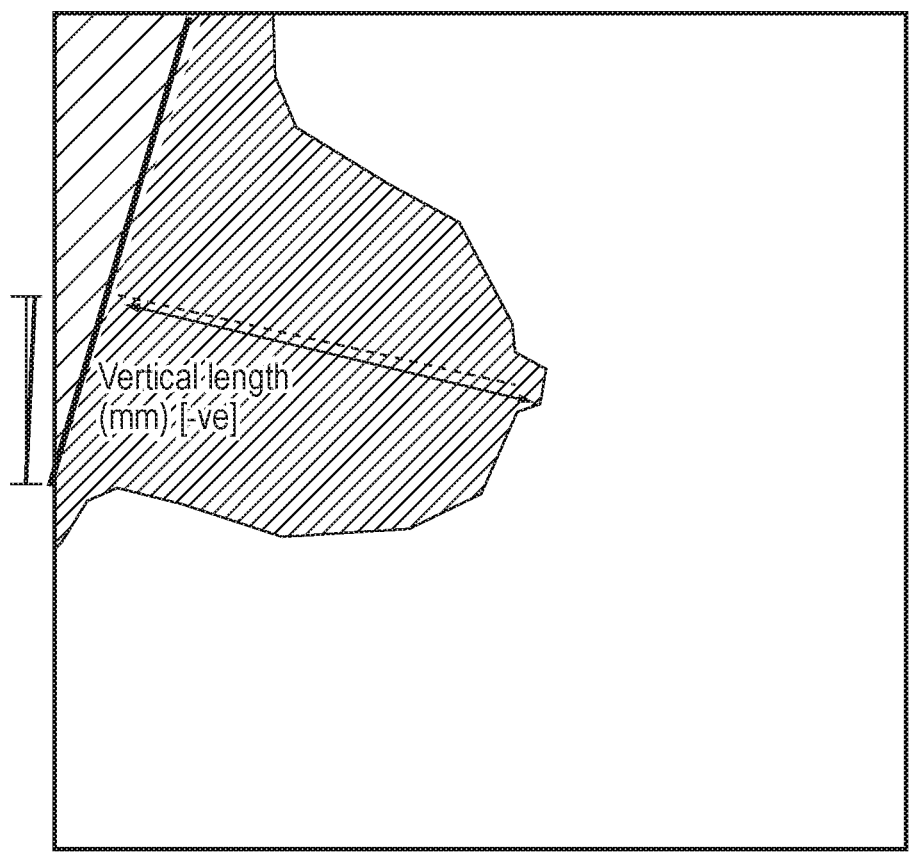
FIG. 13 shows the vertical distance from the posterior nipple line to anterior pectoral edge on an MLO view of a breast connected to a pectoral muscle along the anterior pectoral edge.

Vertical Distance PNL to Pectoral Edge—the vertical distance between the nipple and where the pectoral muscle intersects with the posterior image edge and the intersection of the PNL with the anterior margin of the pectoral muscle or the posterior image edge: the distance is classified as 'Positive' if the inferior pectoral edge is above the level of the PNL; 'Negative' if the pectoral edge extends beyond the level of the PNL. A line showing the vertical length can be seen in FIG. 13.

Figure 14:
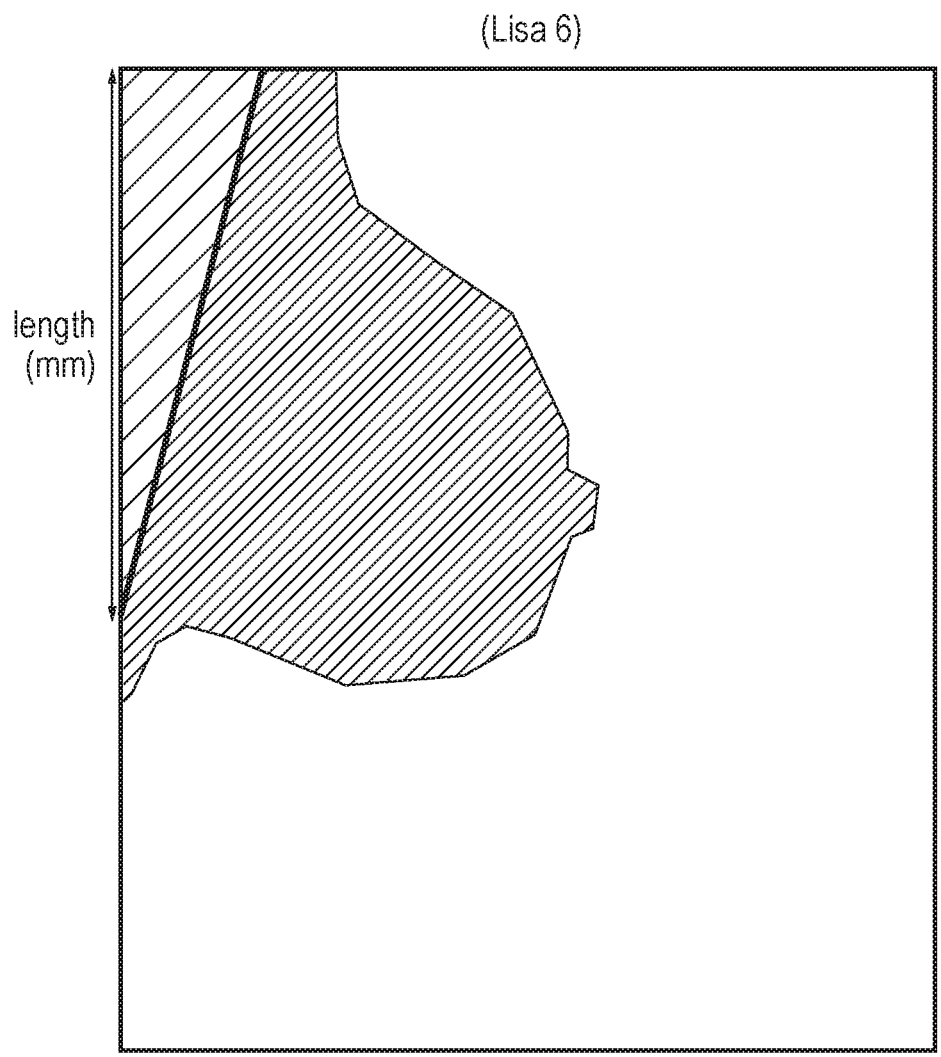
FIG. 14 shows the pectoral muscle length on an image of an MLO view of a breast connected to the muscle.

Pectoral Length—the Pectoral Length is measured from the inferior edge of the image to the superior edge of the pectoral muscle, as shown in FIG. 14. The inferior edge is substantially aligned with the edge of the breast opposite the nipple.

Figure 15:
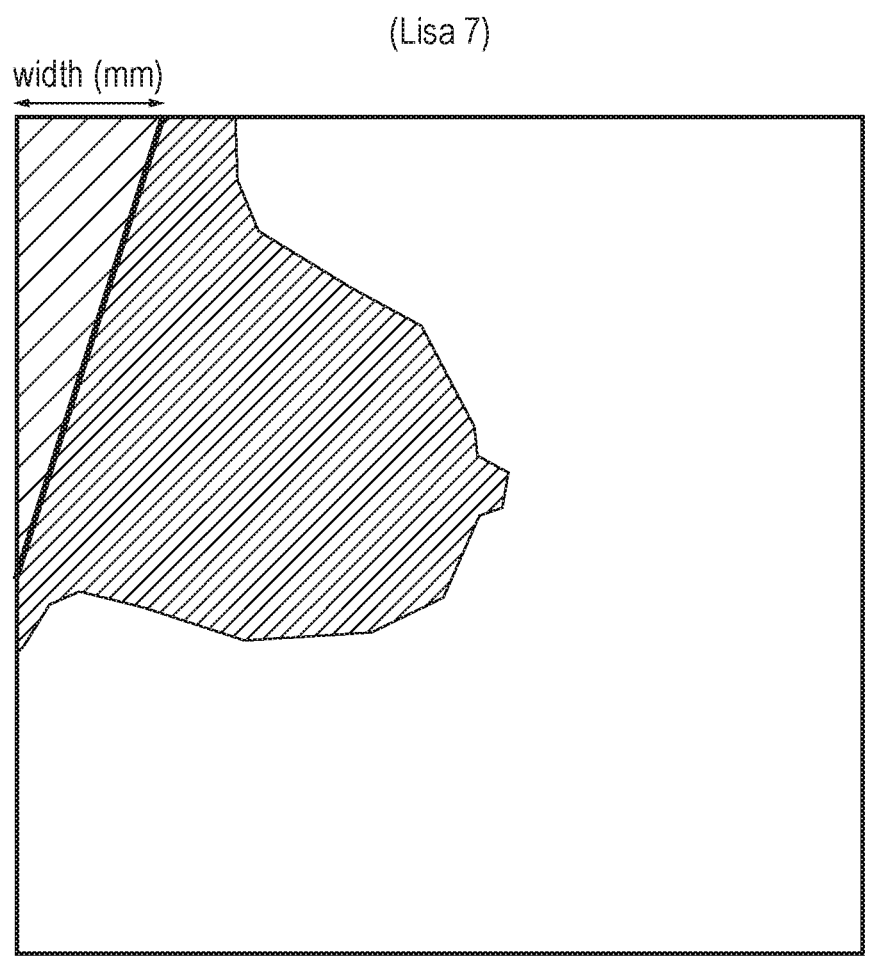
FIG. 15 shows the pectoral muscle width on an image of an MLO view of a breast connected to the muscle.

Pectoral Width—the pectoral muscle width is measured from the posterior edge of the MLO image to the anterior edge of the pectoral muscle as shown in FIG. 15. The posterior edge is normal to the inferior edge and above the breast in the MLO image.

Figure 16:
FIG. 16 shows the pectoral angle theta on an MLO view.

Pectoral Angle—the pectoral angle is shown as angle theta in FIG. 16. It is measured between the pectoral muscle and the breast and the posterior image edge. The pectoral angle may be used as a quality metric to indicate that breast tissue on the MLO image has been sufficiently imaged. For example, a pectoral angle theta in a range of 25 degrees to 60 degrees is deemed sufficient. An angle theta in a range of 35 to 50 degrees is more sufficient.

Figure 17B:
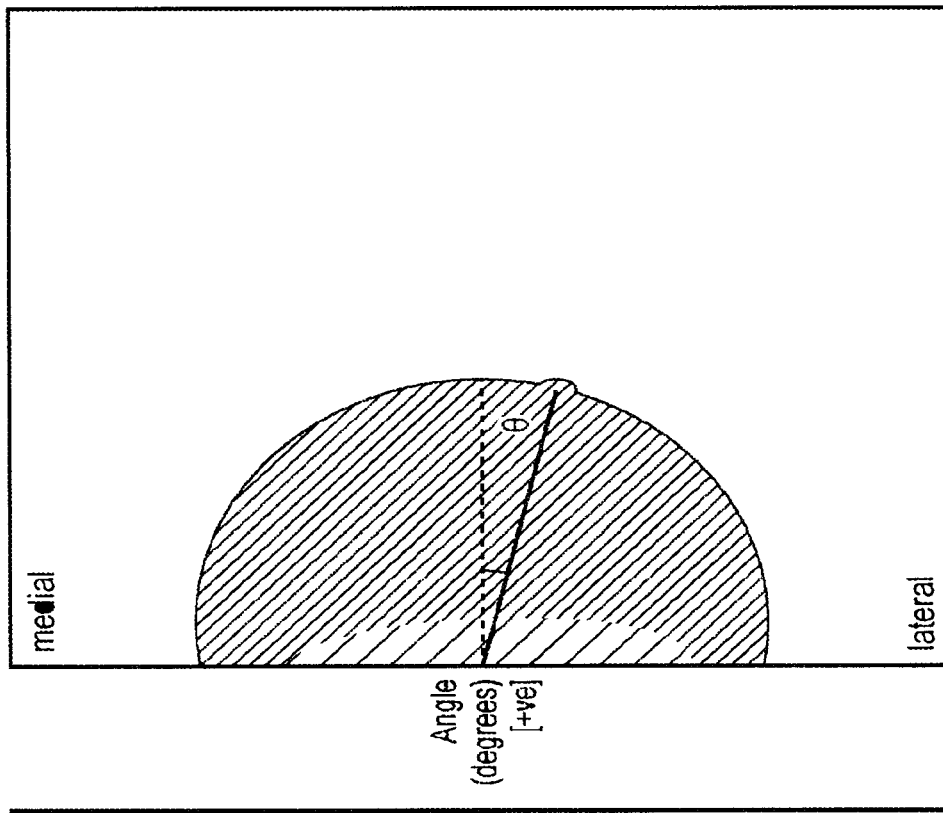
FIG. 17b shows the nipple pointing lateral.
Figure 17A:
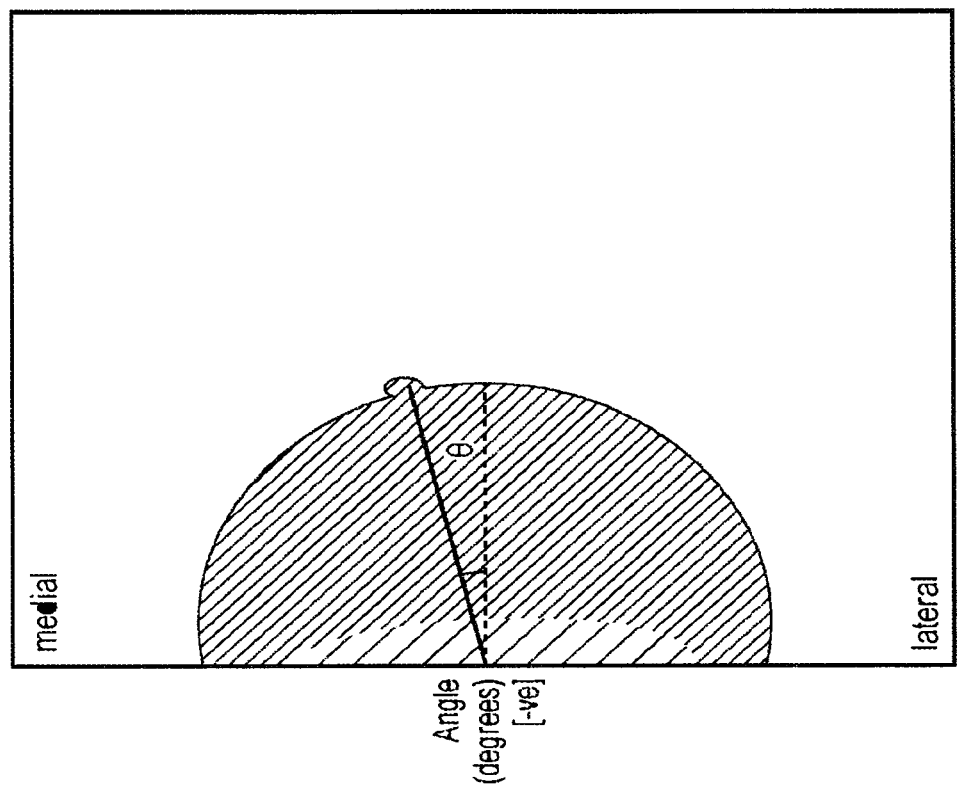
FIG. 17a shows the nipple pointing medial.

Nipple direction—on the CC view as shown in FIGS. 17*a* and 17*b*, the middle of the breast is identified and a first line from the nipple/skin boundary is drawn to that point. A second line, which is shown as horizontal line and which corresponds to the posterior line length shown in FIG. 11, is drawn in the middle of the breast and the angle is computed between the first and second lines. If the angle is 'negative' then the nipple is pointing medial as shown in FIG. 17*a*, and if the angle is 'positive' as in FIG. 17*b* then the nipple is pointing lateral for a lateral nipple.

Figure 18:
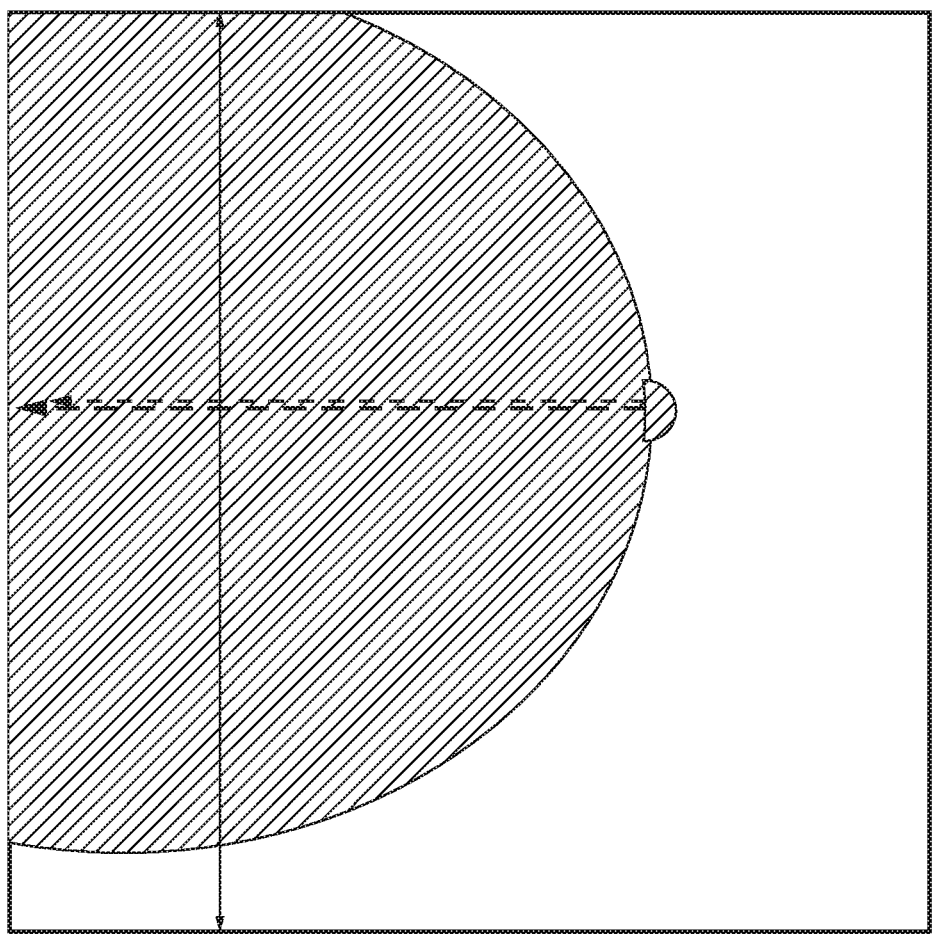
FIG. 18 illustrates dimensions for whether all breast tissue has been imaged on a CC view.

⅓ Rule—a line perpendicular to the posterior nipple line, PNL and parallel to the posterior edge of the image is drawn ⅓ from the chest wall on the CC view. The '⅓ rule' line is shown in FIG. 18. If the skin edge disappears (medial and lateral) at the line or within its margin, then all breast tissue has been imaged.

Figure 19:
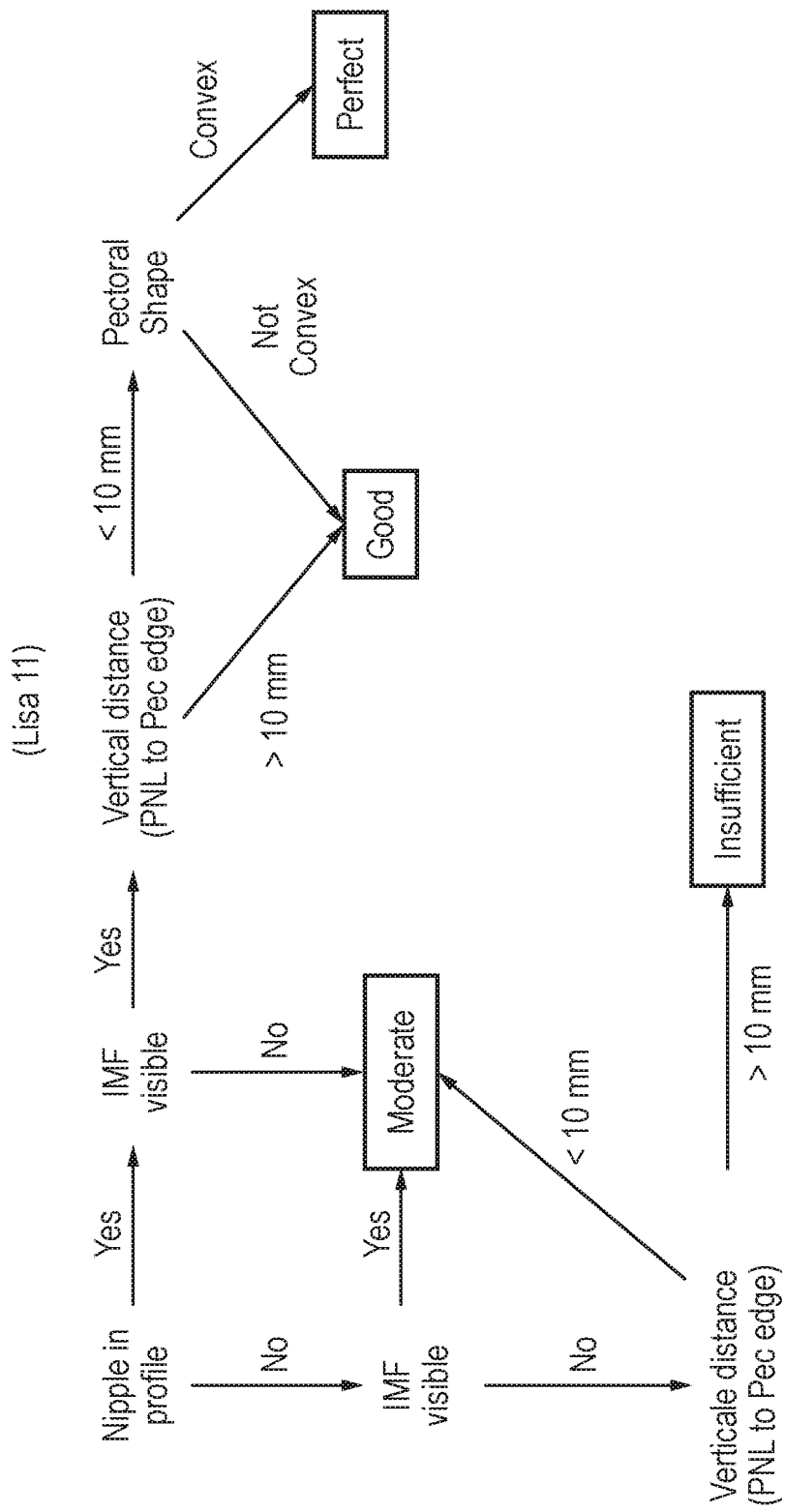
FIG. 19 shows a flow chart to determine positioning score.

MLO Image Positioning Score—A chart showing steps in a method for determining the positioning score for an MLO view is shown in FIG. 19A. The MLO image positioning score may be determined by using the following metrics: Nipple in profile, IMF visible, pectoral shape and vertical distance PNL to pectoral anterior edge. Following the flow chart (FIG. 19) each MLO image can be classified as either; Perfect, Good, Moderate or Insufficient. If any of the individual metrics cannot be computed the overall score will be reported as 'Unknown'.

CC Image Positioning Score—the CC image positioning score is determined by using the following metrics: Nipple in profile, ⅓ rule, PNL difference between the CC and MLO and the nipple angle. The MLO of the same side is identified and the difference in PNL length is computed for the CC. Following the flow chart each CC image can be classified as either; Perfect, Good, Moderate of Insufficient. If any of the individual metrics cannot be computed the overall score will be reported as unknown including if an MLO image of the same side was not taken.

Figure 20:
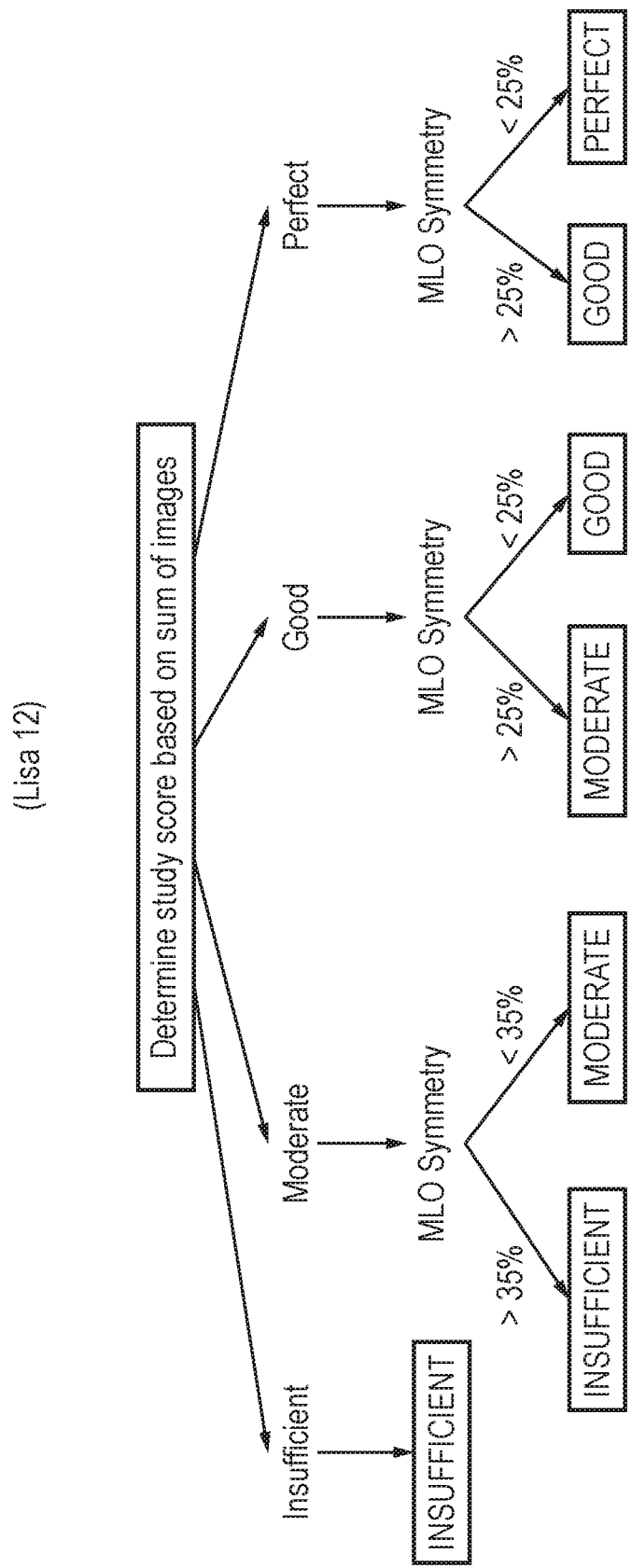
FIG. 20 shows a flow chart to determine a study score from a study comprising a plurality of images.
Figure 21A:
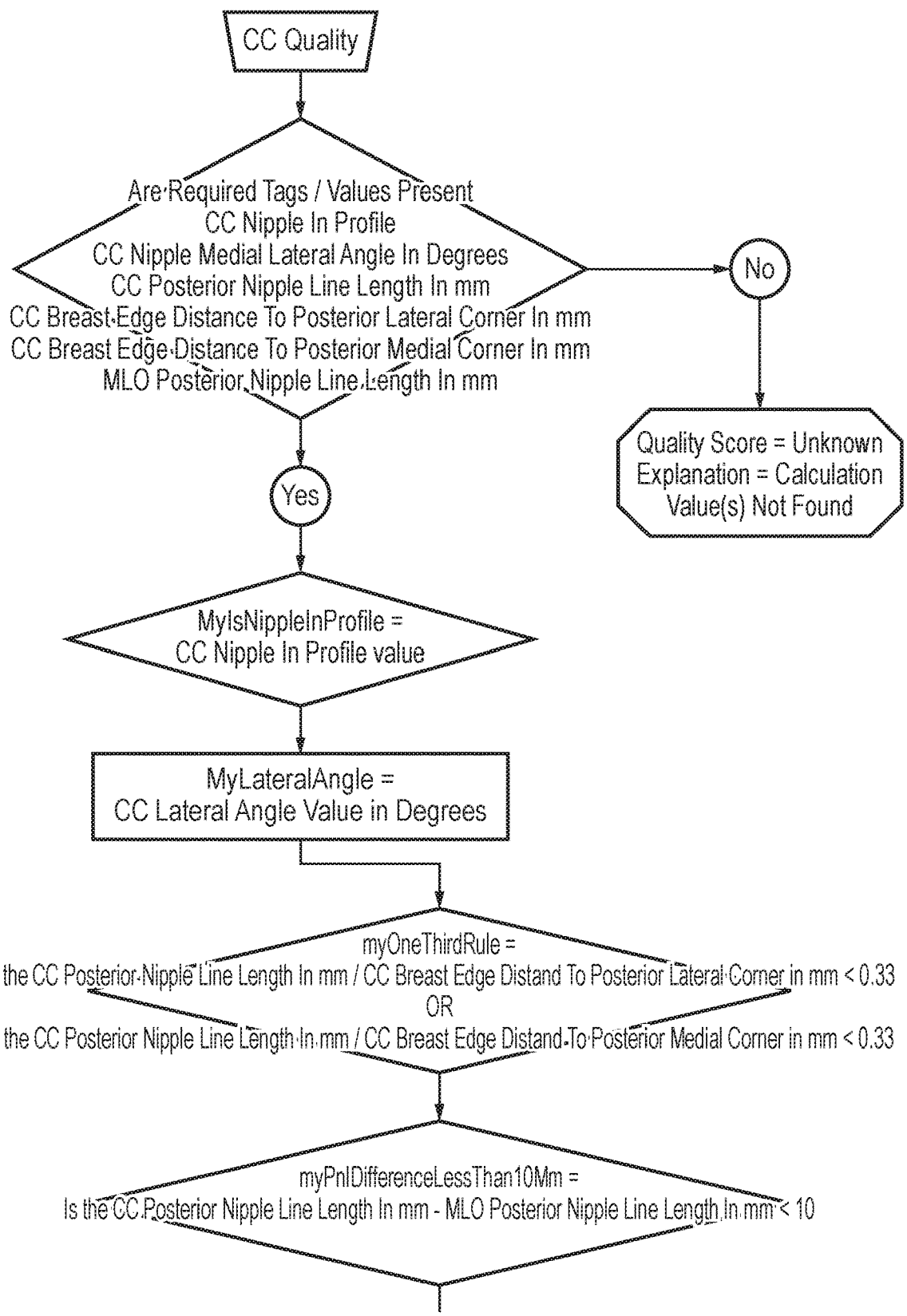
FIG. 21(a), FIG. 21(b), FIG. 21(c) . . . 21(i) illustrates a method for determining a study positioning score.
Figure 21B:
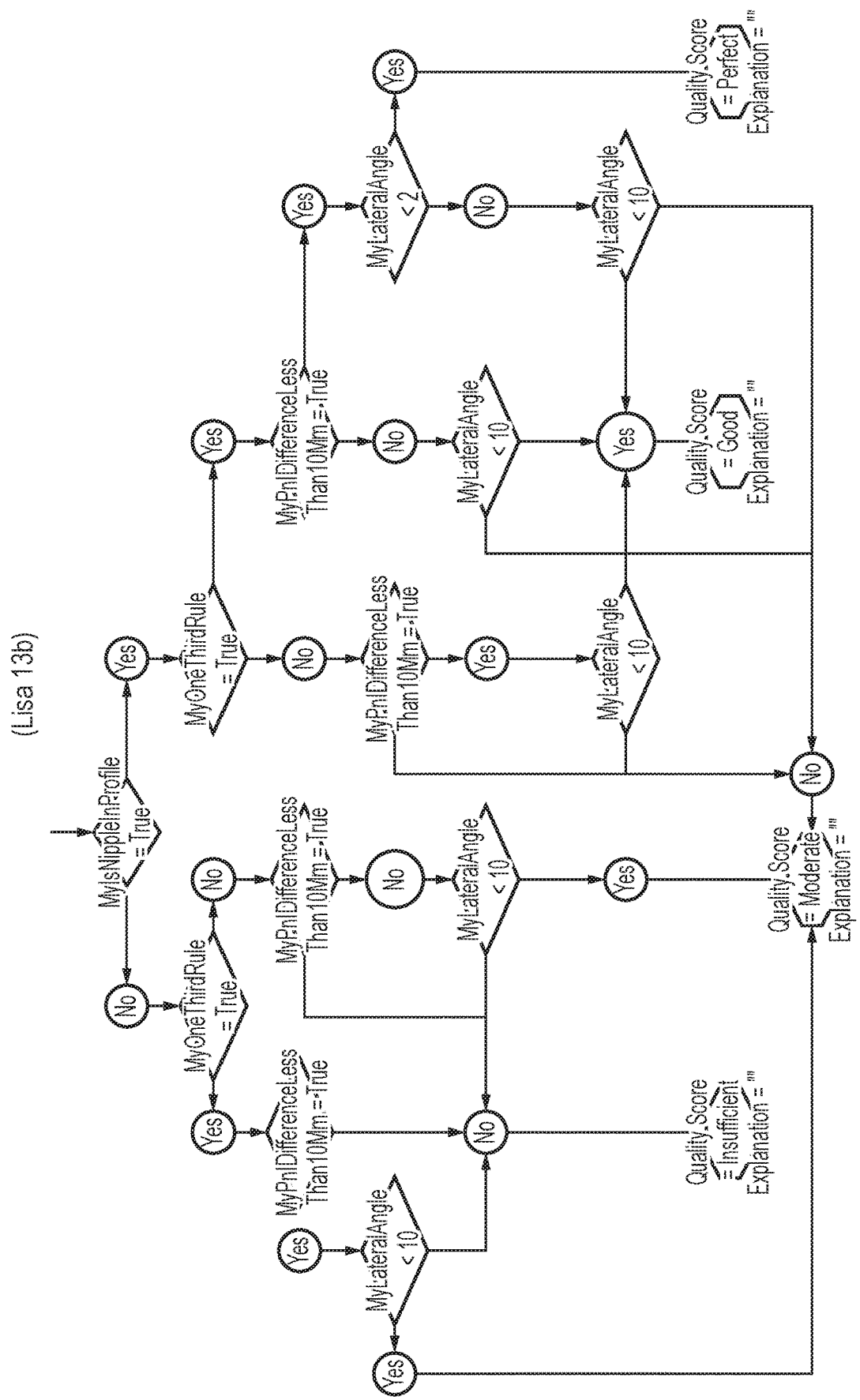
Figure 21C:
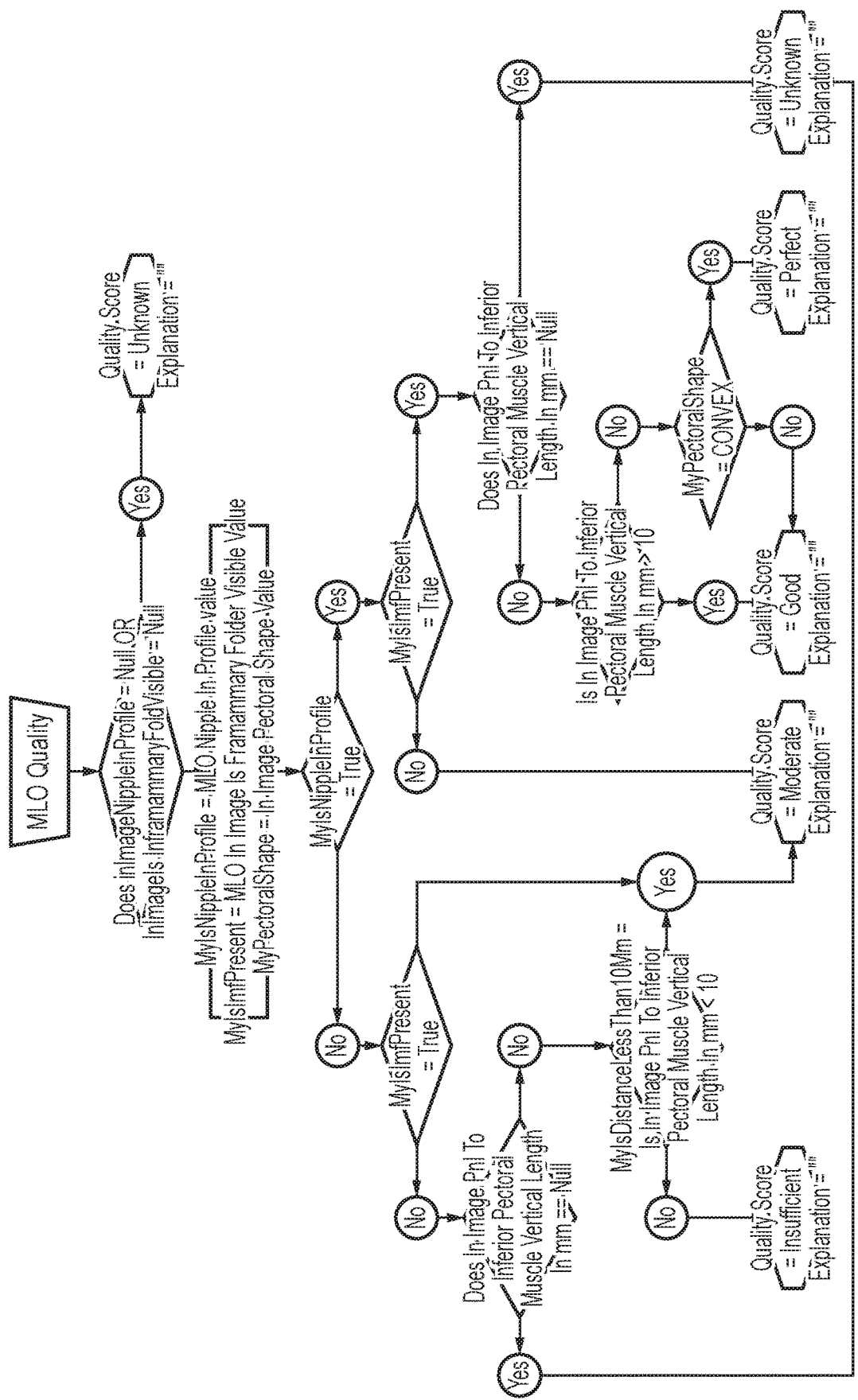
Figure 21D:
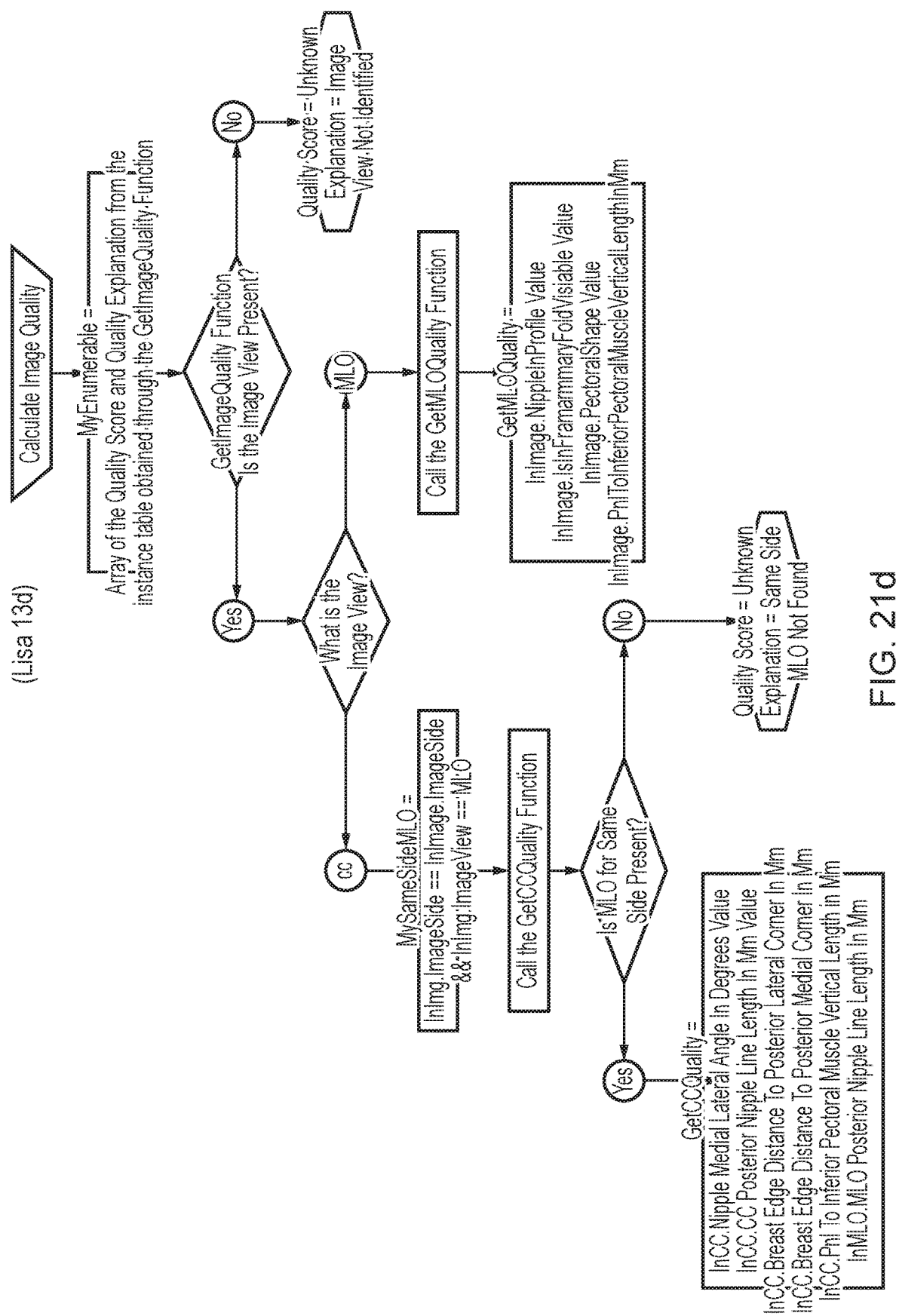
Figure 21E:
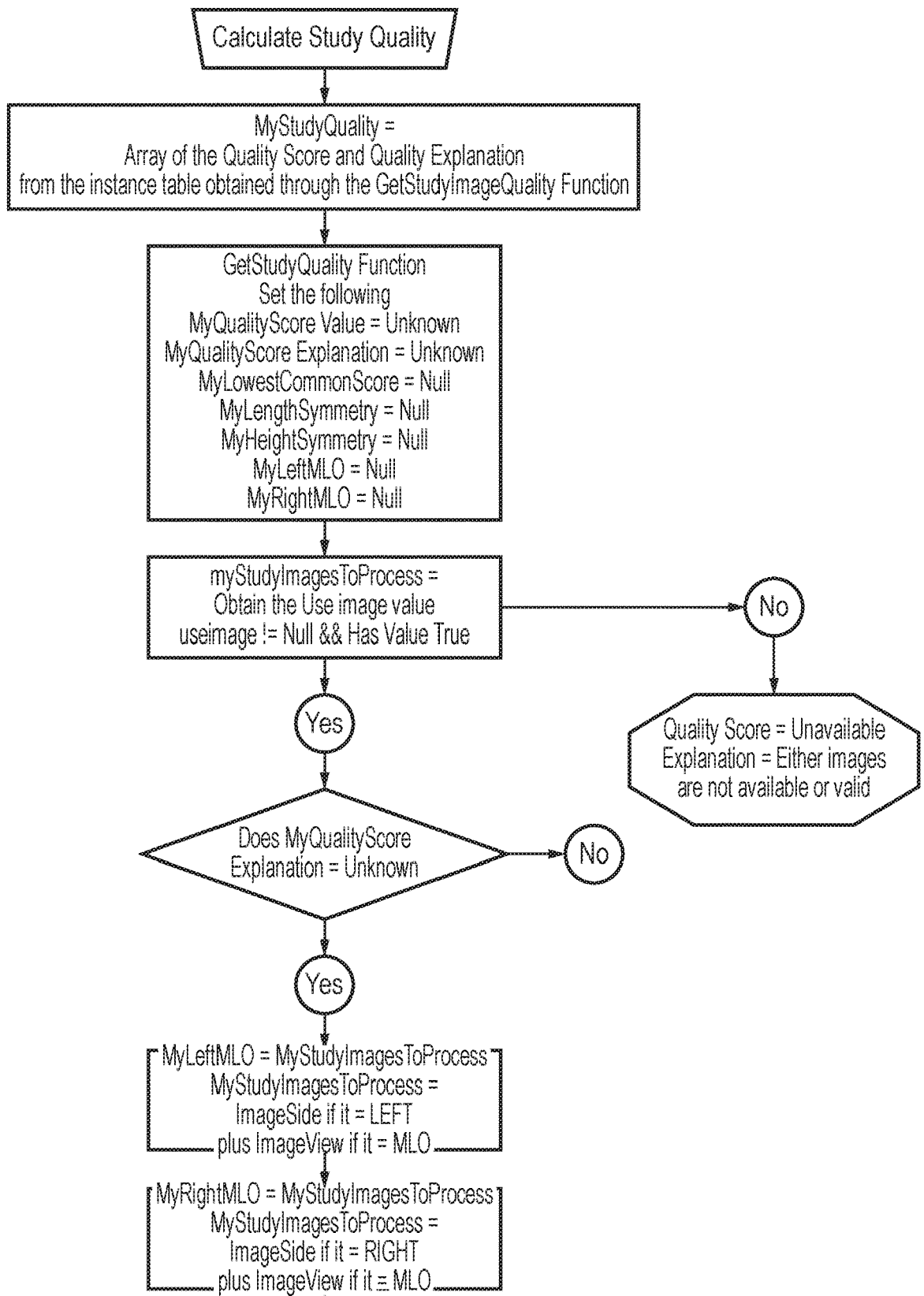
Figure 21F:
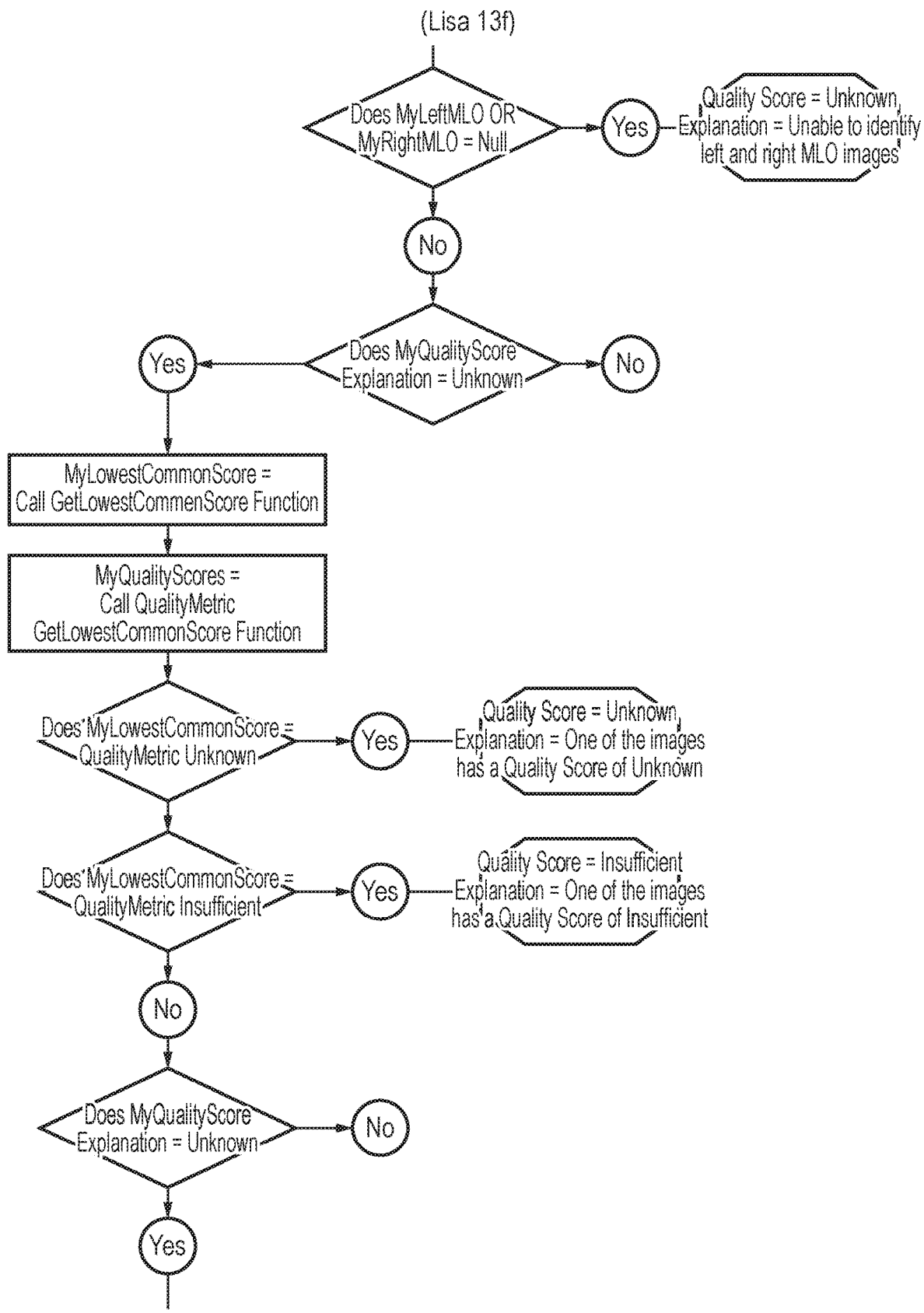
Figure 21G:
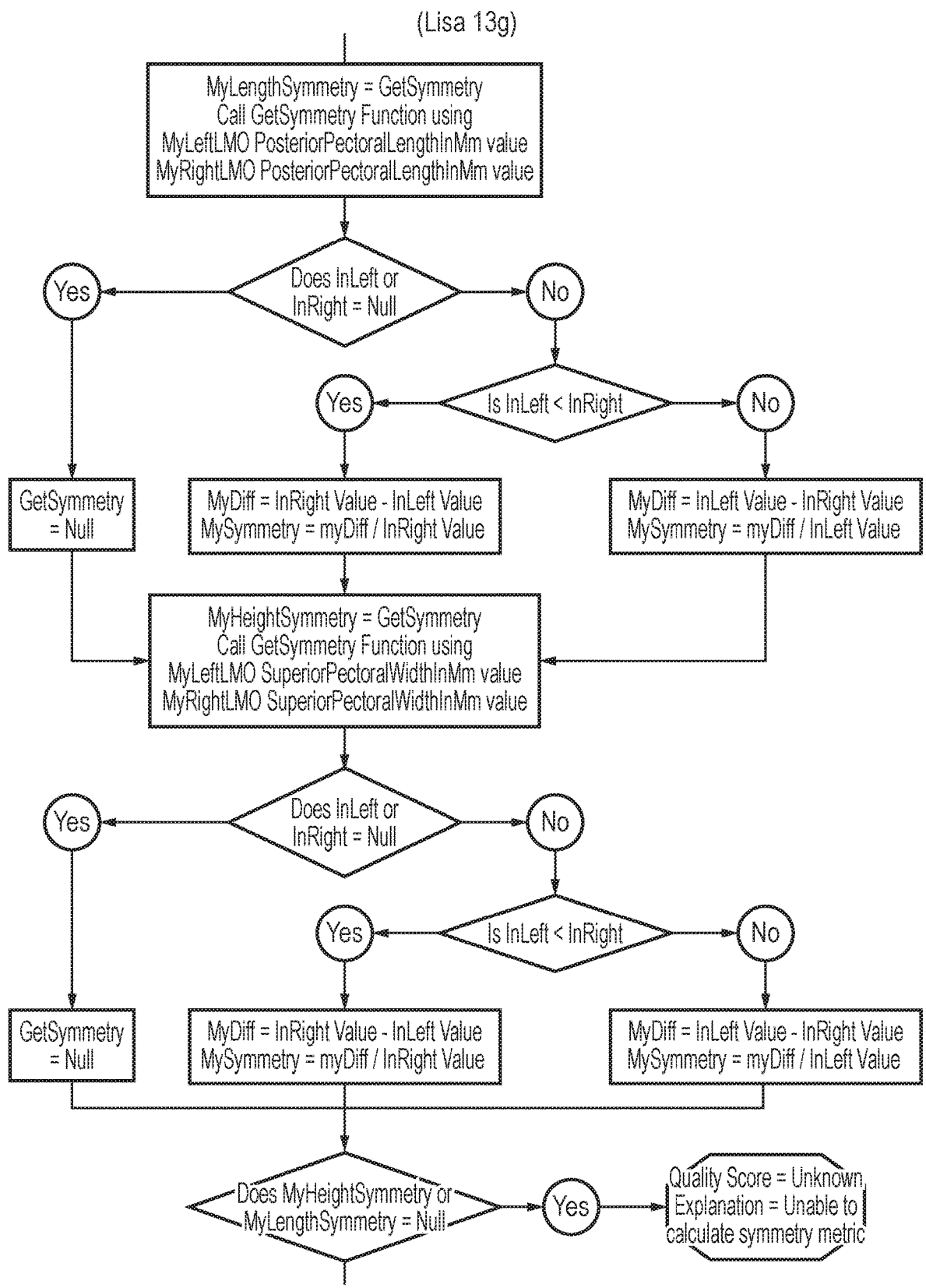
Figure 21H:
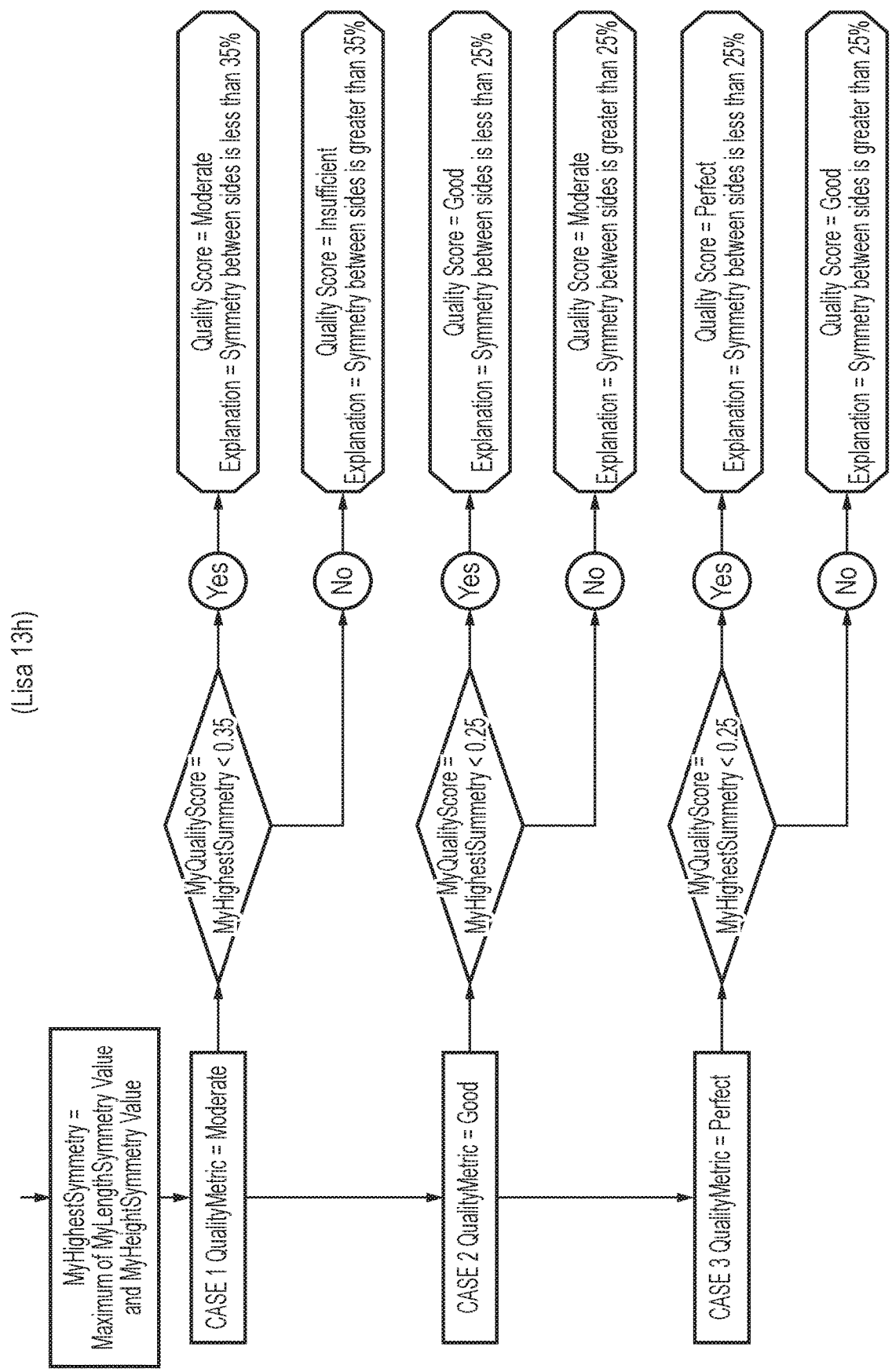
Figure 21I:
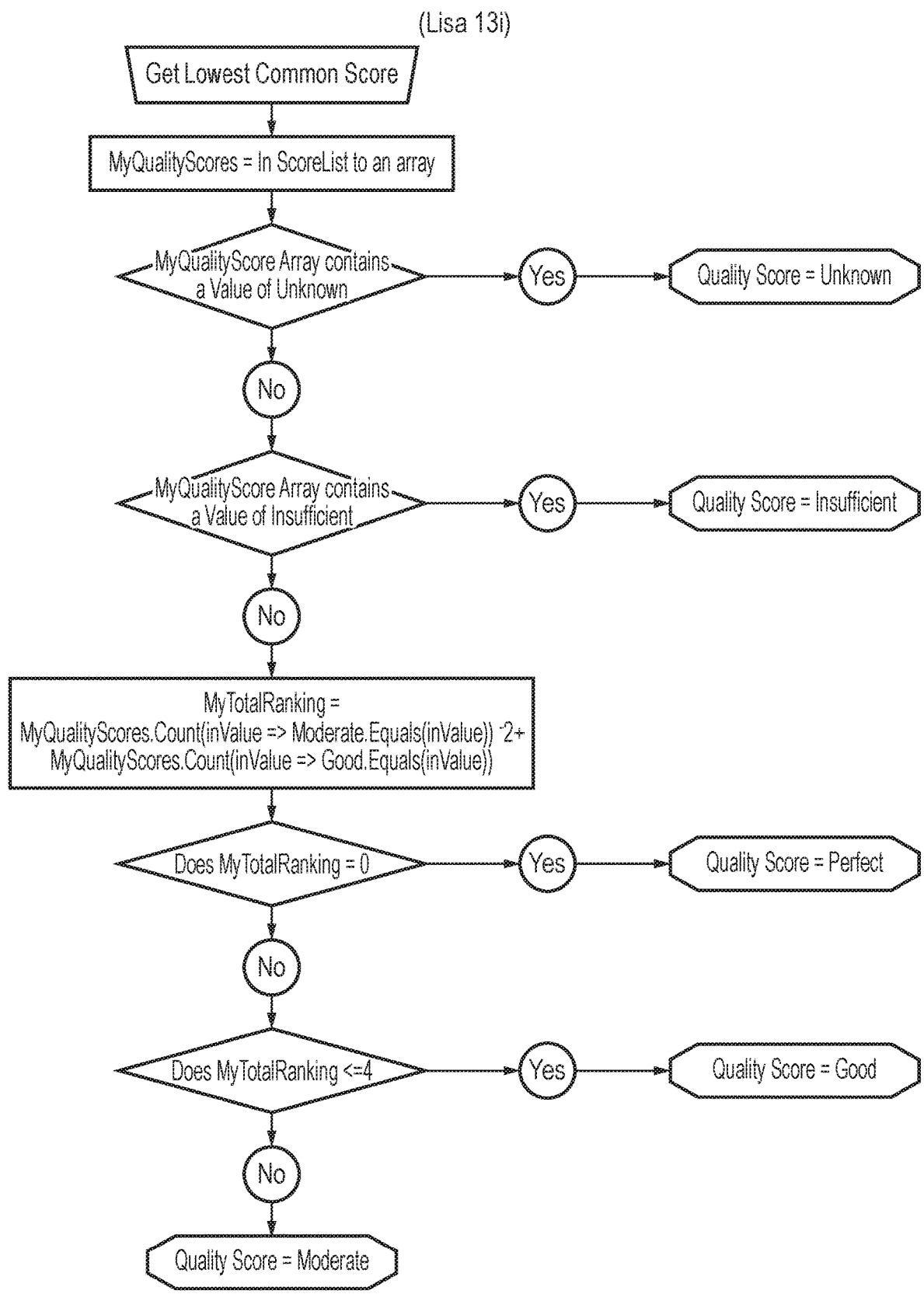

Study Positioning Score—in addition to providing a score for an image, a score for the overall study is also provided. FIG. 20 shows steps to evaluate collective quality of a plurality of images in an overall study. This is based on the individual scores of the study images and the symmetry of the pectoral muscles between the left and right MLO image from determining the difference in the height and width of muscle.

If there are more or less than a specified number of images in a study, for example, 4 images, then the score for the study is reported as Unavailable. If any of the images have a score of Unknown, the study is reported as Unknown. If any of the images are reported as Insufficient, the overall study score is Insufficient. If all 4 images are Perfect, the overall study score is Perfect. For the rest of the images the following numeric values are given based on the image score: Perfect=0, Good=1 and Moderate=2. The sum of the image scores are computed and the following thresholds are applied: Good—at least 4 and Moderate—at least 2 and less than 4. The symmetry of the pectoral muscles in then determined and a final study score is given.

In a preferred embodiment a density score and a density map, provide context for outcome decisions indicated by the positioning score. For example, a fatty breast which has a relatively low density a in the range, or a breast which is poorly positioned in the image may not require a retake or referral for another imaging technique, whereas a dense breast which has a relatively high density which may be determined based on statistical data from the image, data from a test object in comparison with the image, and/or a preselected density threshhold, wherein cancers are harder-to-diagnose, which is also poorly positioned, would require retake or referral for another imaging technique.

The system provides a summary display that comprises at least: a density measure as a percentage of breast volume, other numerical and or letter designation; radiation dose and pressure; indication of risk over a period (either full or abbreviated with option to refer patient for full appraisal). The display also shows facility-recommended appropriate imaging for complete screening (e.g. annual TomoHD, MRI) and by triage based on sensitivity of mammography vs risk whereby the modalities recommended for women are customised depending on the patient's risk profile and sensitivity of mammography in women of a certain breast density. The triage might be based on 'recipes' used by experienced radiologists. Note that the sensitivity of mammography is dependent on the ROC operating point of the 'readers', including the manner in which the images are read, whether single reading, single reading with CAD, double reading, double reading with CAD, double reading with arbitration, and so on.

Figure 8:
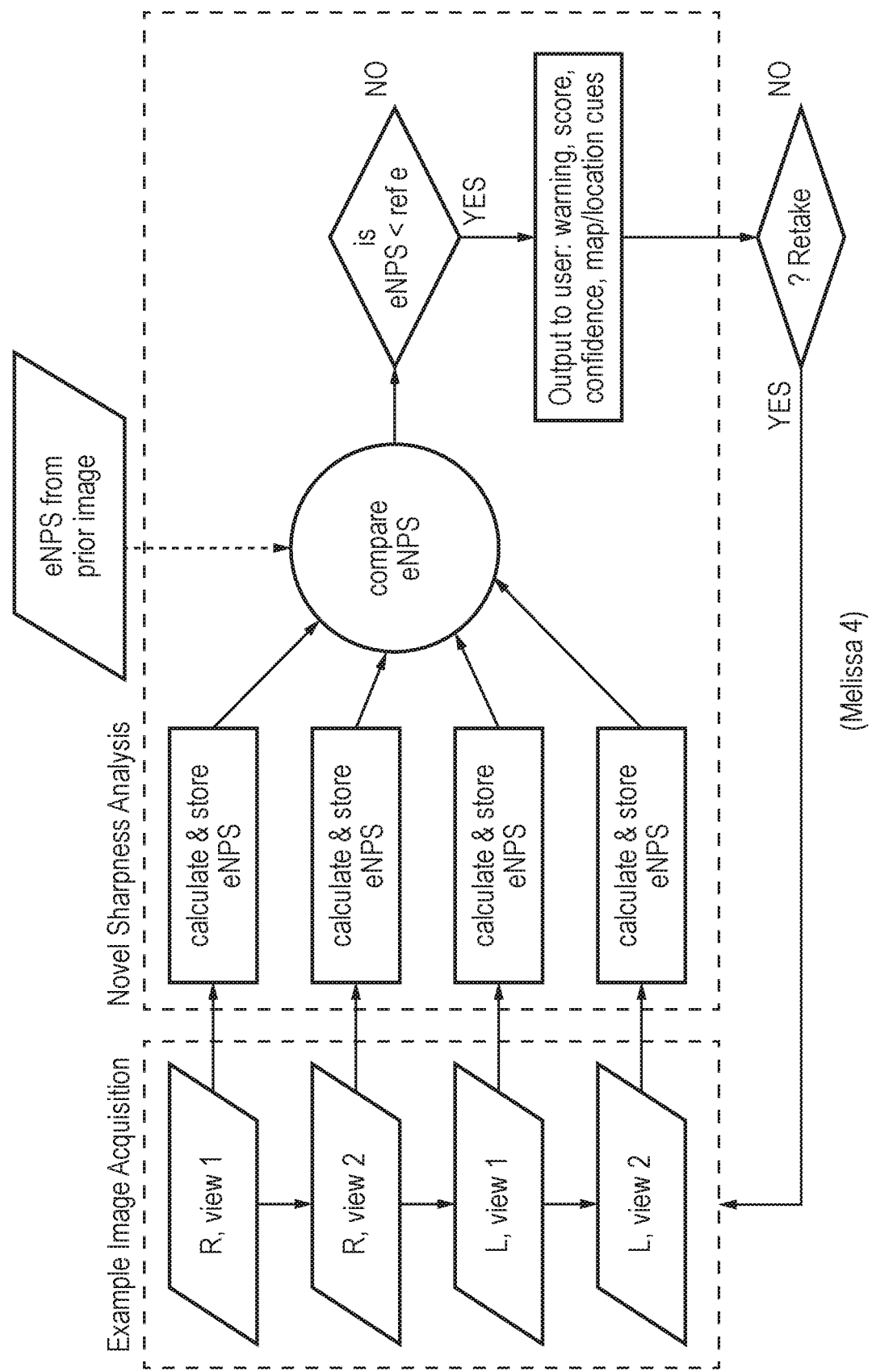
FIG. 8 is a flow chart of a method for user evaluation of quantitative analysis of image sharpness for a comparison of a plurality of images.
Figure 9:
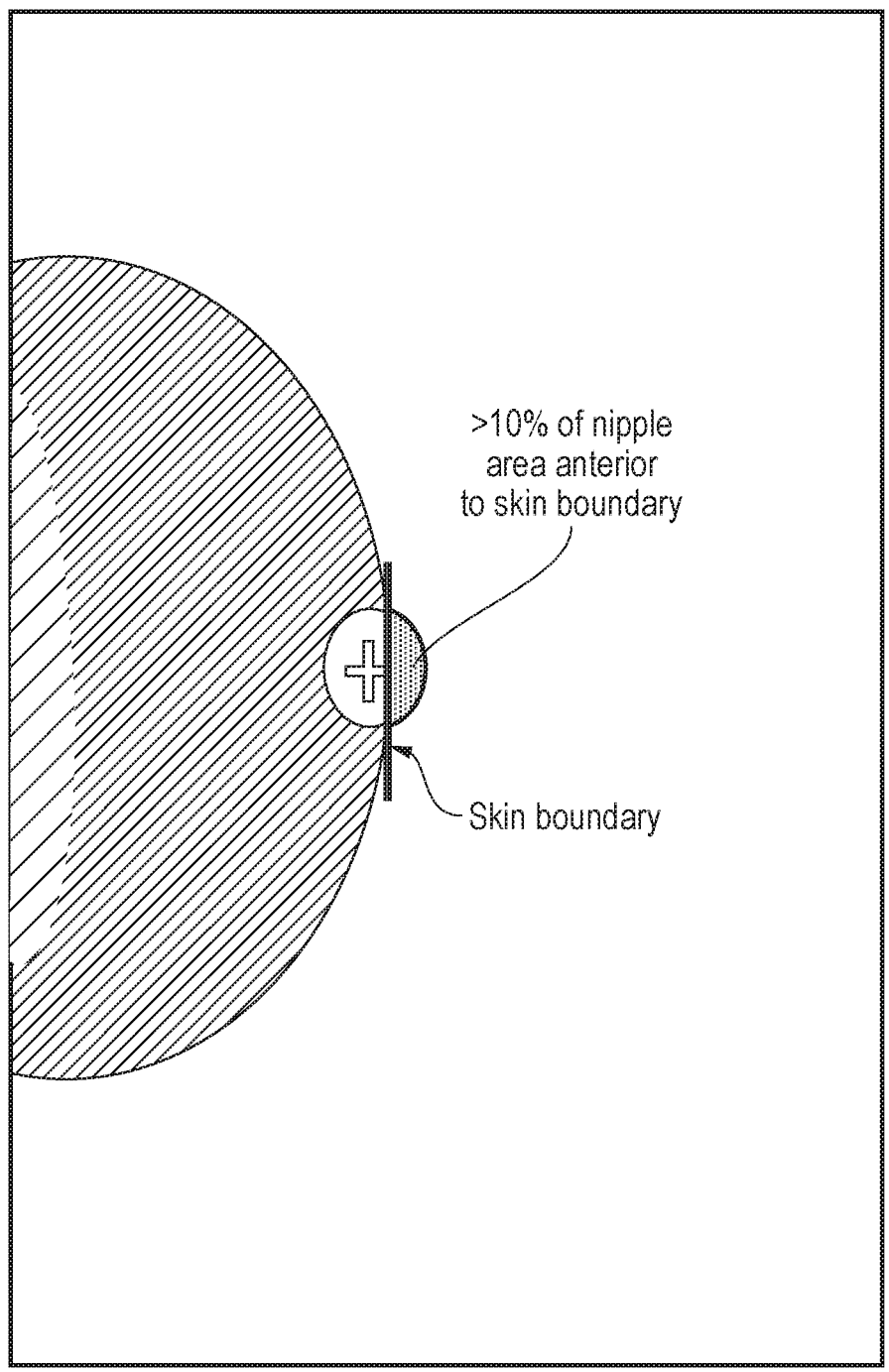
FIG. 9. shows an example of nipple in profile.

The flowchart in FIG. 8 presents an exemplary embodiment of image sharpness measurement and user feedback via a process flow diagram, indicating a potential use of the sharpness detection and quantification method for application with mammographic images. In the exemplary case, an imaging study is performed of right and left breasts in two anatomical views, such as CC and MLO images. The images serve as inputs to the novel sharpness analysis method, where the eNPS is calculated for each image and are then compared to determine images that are sharp or have a comparatively low level of sharpness. Feedback is given to the user via qualitative and quantitative text and/or graphical outputs that report on the potential presence of image sharpness within a metric of sharpness or below a metric of sharpness;

The system further detects and calculates the presence of artefacts and motion caused loss of sharpness among quality assessments. For example:
1. a mammographic image is linearised;
2. a constant thickness region of the breast image is segmented;
3. overlapping, or non-overlapping, ROI are identified from within the constant thickness breast region;
4. the 2D effective noise power spectrum (eNPS) is determined using the region of interest (ROI) extracted in Step 3, such as following Equation 4;
5. an estimate of the noise power spectrum (NPS) is made from the eNPS; and
6. the NPS estimate is integrated over spatial frequencies $f_x$ and $f_y$ from 0 to the maximum sampled frequency to obtain the estimated system noise variance estimate, $\sigma^2$.

Methods to estimate the NPS from the eNPS may include, but are not limited to the following two examples, where the first is as follows:
7. assume symmetry of the 2D eNPS and find its radial average after a transformation to polar coordinates;
8. fit a model (e.g. polynomial function) to an appropriate high frequency region of the 1D averaged eNPS vs radial frequency. The high frequency region is selected such that anatomical noise is minimal (e.g. spatial frequencies greater than 1 mm$^{-1}$), the fitting procedure may need to ignore 'spikes' in eNPS, such as from anti-scatter grid, aliasing;
9. extrapolate the model fit to low frequencies. The fitted function is the NPS estimate. This provides for patient-specific image quality since the model is fit to data derived from at least one image of a specific patient. So patient-specific effects of thickness, soft tissue composition, and especially the density of the specific patient's soft tissue on noise in the image of the patient's soft tissue are taken into account.

Alternatively, NPS might be estimated according to FIG. 5, and could include:
10. in Step 4, a 0th order polynomial (mean value) is subtracted from the image ROI as a first estimate of the eNPS, which includes all low frequency image intensity variations. A second estimate of the eNPS is then made using subtraction of an nth order polynomial, where n is 2 or greater. This second estimate will have removed some of the low frequency signal variations.
11. the two 2D eNPS from Step 10 are compared, and eNPS values with a significant difference are discarded from analysis based on the assumption that they represent noise power contributed by normal anatomy. Whether the difference is significant is determinable by a statistical test, which provides an indication of the difference in comparison to a preselected value. For example a paired T test is applicable and the difference is significant for p values less than 0.05 as a standard, although other p value thresholds such as 0.02 and 0.08 are could be set either by an operator of the image taking apparatus or a remote user connected to the same Cloud as the system.
12. interpolation (multiple approaches to interpolation may be used) is performed to estimate the eNPS at the spatial frequencies with missing values after Step 11. The result is the NPS estimate.

This method provides an NPS estimate that is patient specific. Traditional methods are not patient specific. A traditional method of noise measurement is based on uniform image of a test object in which only a stochastic signal is required. A traditional method example is the EUREF CNR calculation, or for a direct implementation of Equation 4.

Compared to other prior art that finds uniform regions in an image (not applicable to mammography, but useful for CT), or only includes high frequency noise, the present method is method is more accurate because it includes estimates of low-frequency noise sources.

While the absolute value of the noise variance could be presented to the user, the relative noise may be a more useful measure to allow for comparison between imaging systems. The relative noise is obtained by a normalisation step as follows:
13. normalised noise may be obtained by dividing the estimated variance from step 7, $\sigma^2$, by the square of the mean linearised image intensity from within the region of analysis.

Figure 6A:
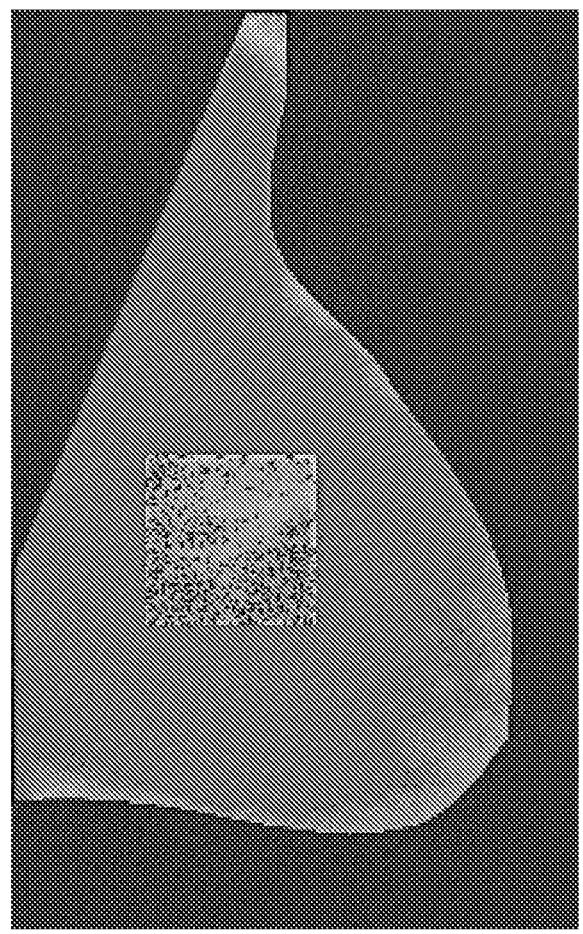
FIG. 6(a) demonstrates selection of a central ROI from a digital mammogram to be used for contrast analysis.
Figure 6B:
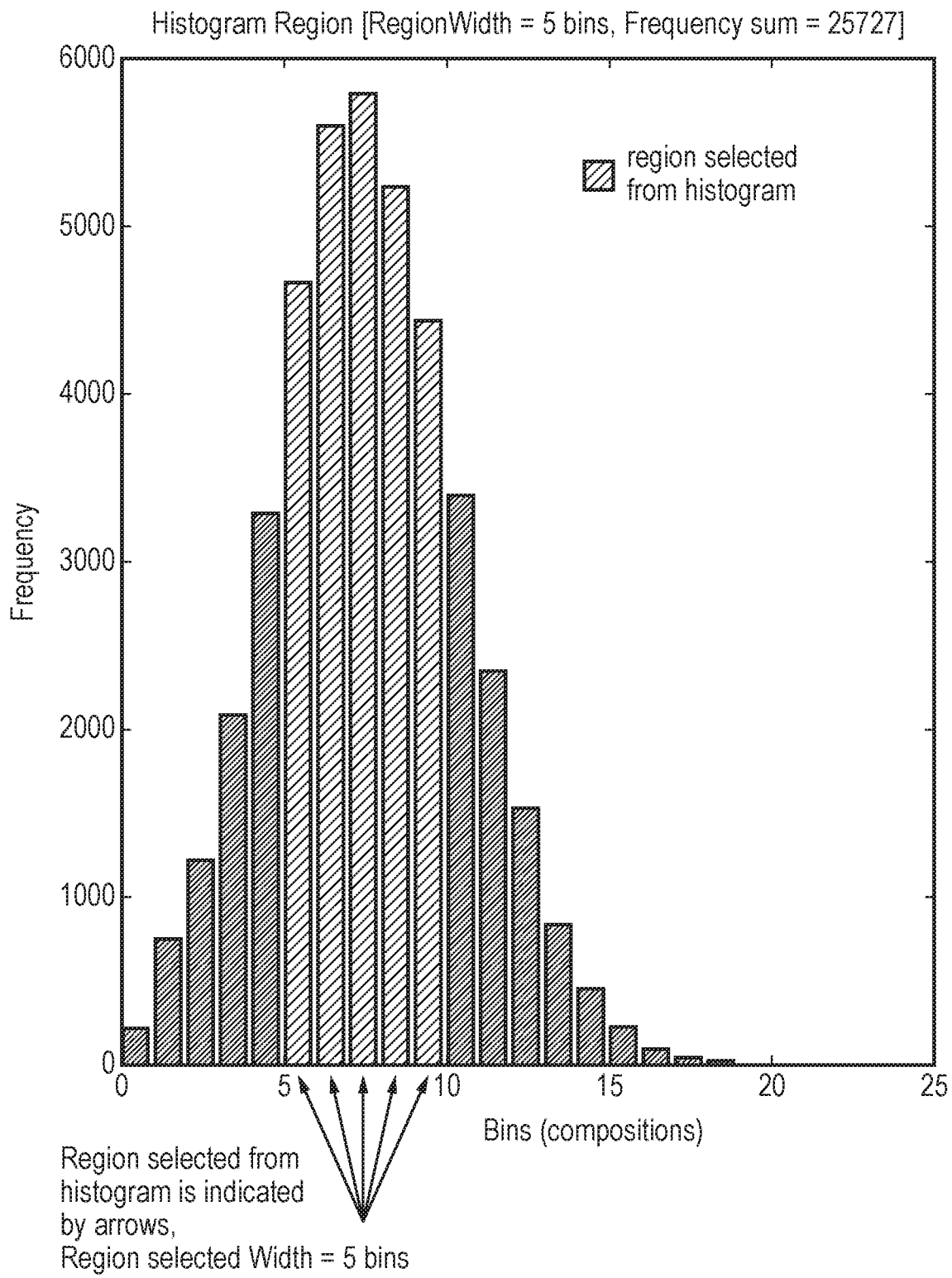
FIG. 6(b) shows a tissue composition histogram of the pixels in the breast density map that correspond to the ROI location in (a) in which pixels in the breast density image within the ROI are identified according to their breast composition and pixels in the ROI are sorted into bins of density tissue composition.
Figure 6C:
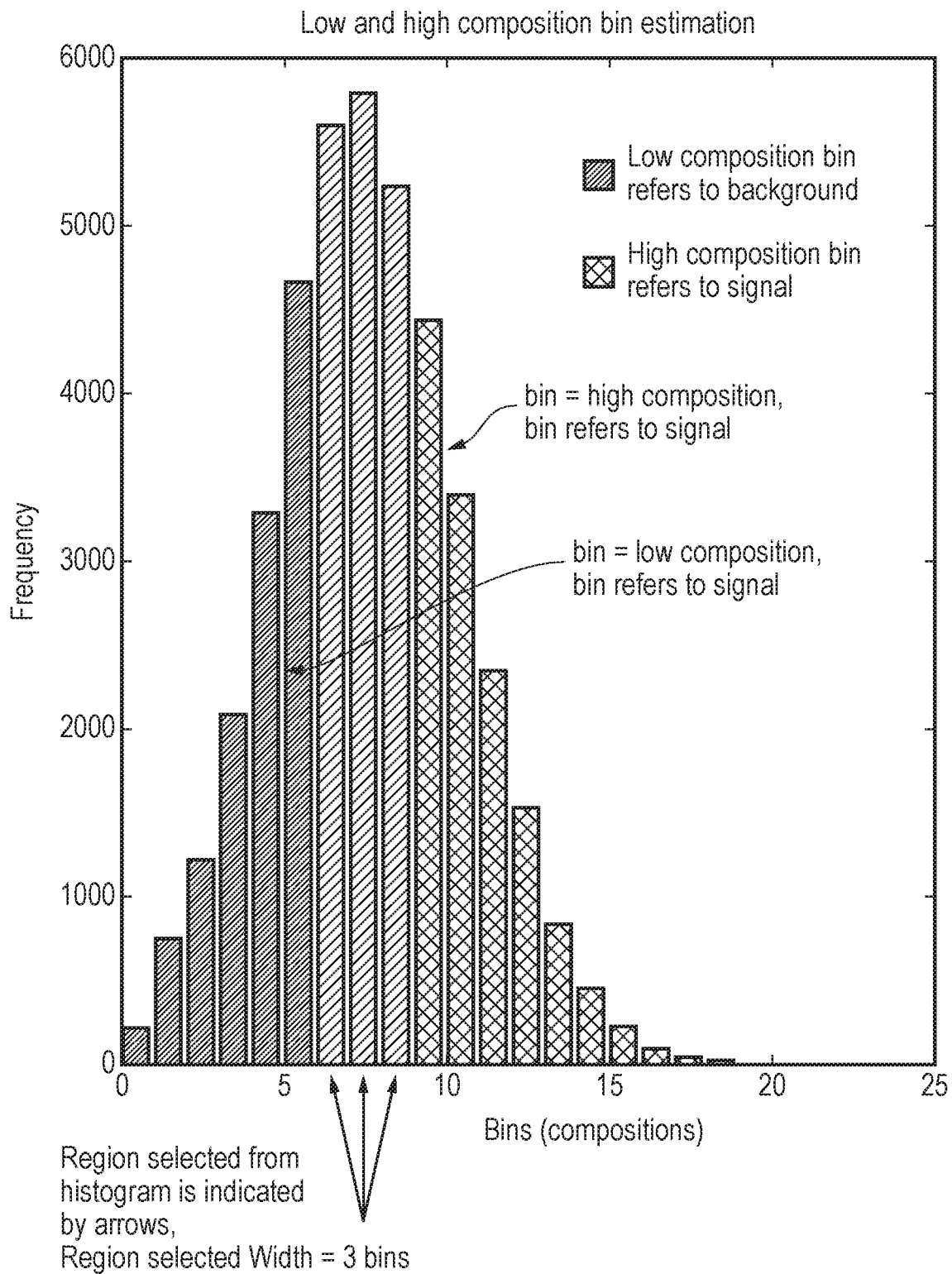
FIG. 6(c) demonstrates selection of tissue compositions that represent an object (yellow) and background (red). The image contrast is calculated as the difference between the mean pixel intensities of those within the ROI that are associated with the object and background composition bins.

In a further embodiment such as illustrated in FIG. 6, the present invention comprises quantitative analysis of image contrast, whereby:
14. a breast density image is generated, using, for example Volpara® Density (note that spectral imaging methods, not limited to dual-energy, triple-energy, or images from photon-counting systems could be used to determine tissue composition); and
15. one or more ROI are selected from within the breast boundary for contrast analysis. Such ROI could encompass the entire breast region, but a preferred embodiment uses a centrally located ROI such as that shown in FIG. 6a and
16. pixels in the breast density image within the ROI selected in Step 15 are identified according to their breast composition, which could include sorting the pixels into histograms, as in FIGS. 6b and 6c; and
17. 'low' and 'high' density tissue compositions are specified according to a composition-difference (e.g., width in number of bins on the histogram) of interest
18. pixels within the ROI from Step 15 that correspond to the 'low' and 'high' density pixels from Step 17 are identified in the original mammographic image under analysis; and
19. the image intensities from the 'low' and 'high' density pixels are determined. For example, calculation of the mean of the image pixel intensities can be performed; and
20. the 'low' and 'high' density mammographic image pixel intensities from Step 19 are used to compute the image contrast, such as by using 6c, where either the 'low' or 'high' density intensities could be defined to correspond to background and object intensities, respectively. Alternatively, a relative contrast can be computed by dividing the results from Equation 1 by the background image intensity. Correlated noise is thereby removed, and the source of loss of sharpness that creates a correlation between pixel intensities and background noise and signal noise is reduced.

In a further embodiment, the present invention comprises quantitative analysis of the image CNR, whereby:
21. the image contrast determined from Step 20, and the image noise determined from Step 12 can be combined using a variation on Equation 5, in which the object noise is omitted from the calculation given that the image noise from Step 12 is assumed to be a reasonable approximation of the background noise for the contrast detection task.

Following this approach, the CNR Equation becomes the following:

Measurements of contrast, noise and/or CNR can be made on multiple views of the breast, such as those described in PC T/GB2014/000217 and improvements thereto. In imaging studies with multiple image acquisitions per anatomical view, such as breast tomosynthesis, dedicated breast CT or contrast-enhanced mammography/tomosynthesis/CT, the noise, contrast and CNR measurements are made on each projection image, or on slice images from a reconstructed image volume. Measurements made from different anatomical views and/or different angular projections could be used to compare image contrast, noise and/or CNR within a study and may help to identify views that should be repeated due to poor image quality.

In a further embodiment, the present invention comprises quantitative analysis of image sharpness, with an exemplary implementation illustrated in FIG. 8, whereby:

22. the eNPS is calculated for each image in a patient study, such as following Steps 1 to 4
above. However, compared to the noise analysis, note that sharpness evaluation does not strictly require that the image analysis region be of uniform thickness. In this application the signal must be relatively uniform across the analysis region, but this could be achieved using image correction procedures such as peripheral equalisation such that sharpness can also be evaluated towards the skin line.
23. all eNPS are compared over a specified spatial frequency region, such as over 1.4 to 2.5 $mm^{-1}$ as suggested by research on spatial frequencies important for visual detection of motion caused loss of sharpness in mammograms. The image with the highest eNPS in this region is defined as a sharp image reference. Note that any available prior patient image eNPS could be included in this comparative analysis.
24. images with eNPS significantly different than the sharp reference over the spatial frequencies of interest are classified. Whether the difference is classified as significant being determined by comparison to a a metric determined from the image, a test object image, and data of the apparatus taking the image.
25. the difference of step 24 between the eNPS of the image with a high level of sharpness and the image with a lower level of sharpness is used to calculate a measure of sharpness magnitude and the confidence in the level of sharpness in the high and low level sharpness images.

Figure 7A:
FIG. 7(a) shows a sharp Right CC (RCC) image mammogram.
Figure 7B:
FIG. 7(b) shows an unsharp Right MLO (RMLO) image mammogram of the same breast as the RCC view in (a)
Figure 7C:
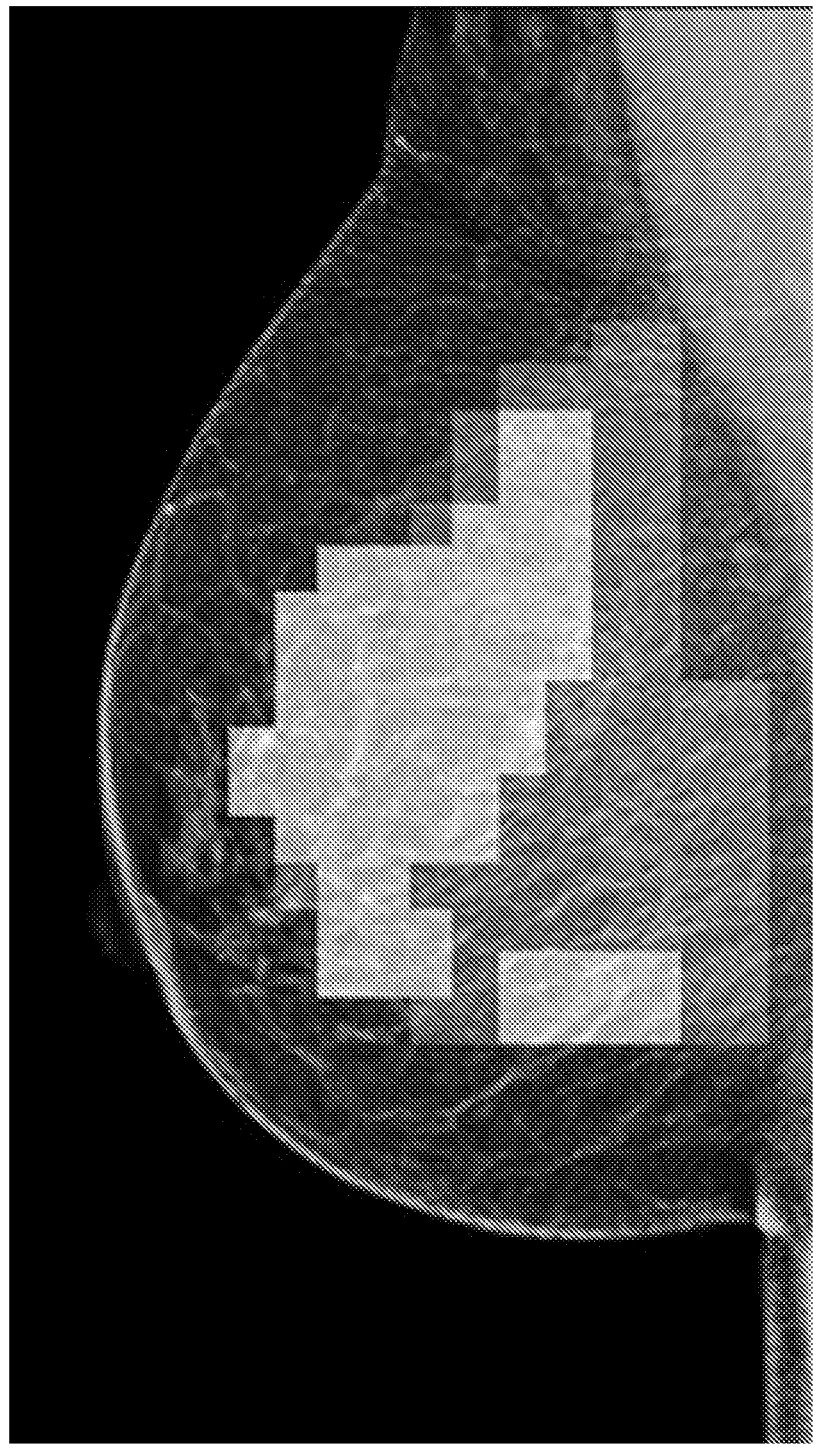
FIG. 7(c) presents the RMLO view from (b) with unsharp areas indicated by white-shading.
Figure 7D:
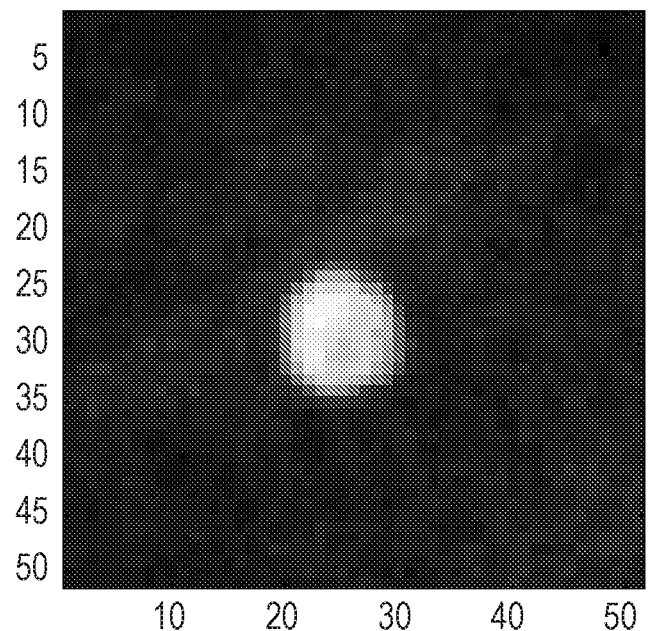
FIG. 7(d) is a region extracted from the RCC image with a calcification.
Figure 7E:
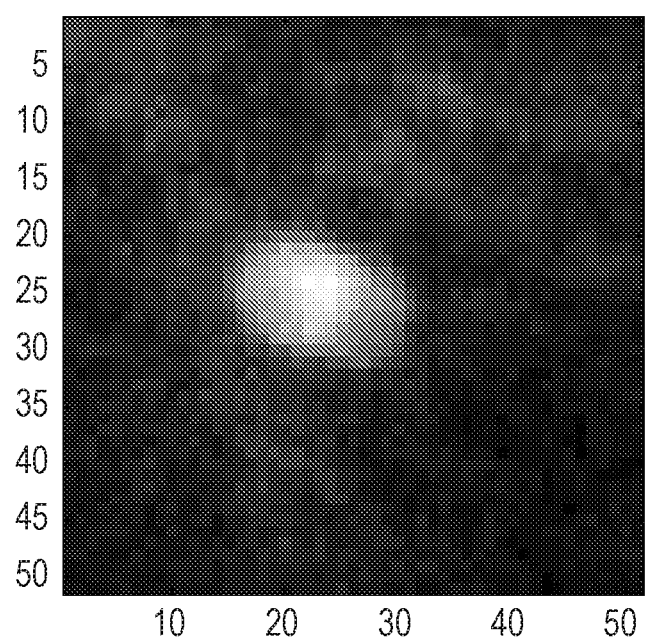
FIG. 7(e) depicts the same calcification as in (d), but in a region extracted from the MLO view, which has an unsharp appearance due to motion of the beast while the image was taken.

In a further embodiment, measures of noise, and/or contrast may be used in combination with the eNPS analysis to quantify image sharpness. In an extension of the above sharpness embodiment, maps of the location of image sharpness below a metric or in a metric range, such as the example shown in FIG. 7c may be prepared, and quantitative measures of sharpness made, whereby:

26. the eNPS may be calculated for each ROI under analysis; and
27. the image eNPS can be compared per-ROI to the sharp image eNPS defined under step 23.

ROI with significantly different eNPS are stored for later use in reporting sharpness of the image with respect to location in the image where there is a low level of sharpness. A decision on whether is difference in eNPS is significant is made by a statistical test, such as a paired T test, and significance is reached when p<a preselected value. Examples of preselected values are 0.02, 0.05, 0.1, or 0.5.
28. the ROI locations from Step 26 are used to prepare a sharpness map that can be used for visualization of the image areas where sharpness is below a preselected level or where confidence in sharpness is below a preselected level, and/or that can be used to prepare text-based cues that suggest a specific image region which should be reviewed for the presence of sharpness low level of sharpness or confidence therein.
29 the unsharp image ROI identified in Step 26 can be used to calculate metrics that quantify the amount of sharpness in terms of image area, including the absolute area of the image below the sharpness metric or in a range of the metric and the percent of the image area having sharpness below the metric or in the metric range relative to the total image area under analysis.

Low level of sharpness is reported in terms of an overall score relating to the magnitude of the eNPS which takes into account spatial frequency information as in step 23. A range is applied to the score determine clinically significant level in sharpness.

These image sharpness quantitative metrics and qualitative output support a decision of whether or not a technical retake of the images should be performed. The sharpness analysis data can also be archived for future use, and can be applied to derive image quality performance metrics on sharpness for quality monitoring, which may include individual radiographers, imaging systems, compression paddle types, etc.

In an embodiment the quantitative noise, contrast, CNR, and/or sharpness results are ordered, and/or scored and/or grouped into categories that relate to image quality and diagnostic performance. These results can be reported for each patient and can be used together with those from other patients to monitor system, operator and/or collective imaging centre performance.

In a further embodiment the results of quantitative image quality analysis, including noise, contrast, CNR, and sharpness are then input into predictive models of diagnostic performance.

In a preferred embodiment the above metrics of noise, contrast, CNR and sharpness be calculated automatically upon input of the clinical image(s) under analysis, so that rapid feedback on image quality may be obtained.

A further feature is an indication of whether a low level of sharpness is occurring in a region of high density and the alert for the radiographic technologist of a 'serious' note, as there may also be a risk of masking and provide a copy of the image with a quantitative or relative indication of the density on the image and indicate where there is a risk of masking on the breast image.

The status 'close of study', may comprise an all-encompassing study score, entailing for example a comprehensive positioning quality score and score on sharpness. On appraisal of the qualitative criteria and related physics data, the radiographic technologist is provided with the relevant quality metrics and can then decide whether to accept the image, or to reject the image and describe the reason for the rejection, including but not limited to artefact (air gap), artefact (skin fold), artefact (other), body habitus, compression, equipment failure, exposure, patient motion, image of test object, positioning (nipple), positioning (pectoralis), etc.

Figure 3:
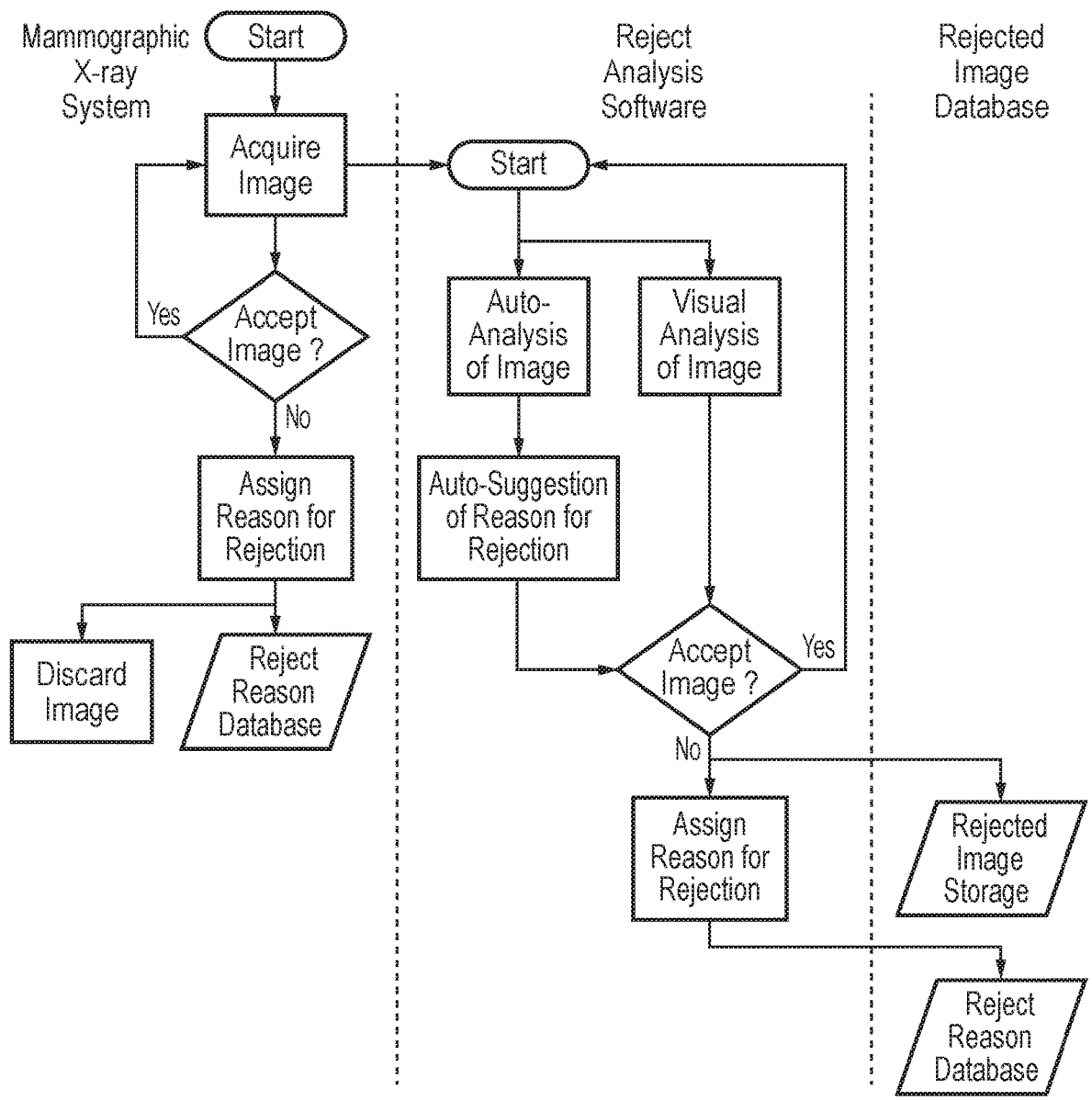
FIG. 3. shows inclusion of external reject analysis software with data collection for post-analysis and technologist re-training.
Figure 4:
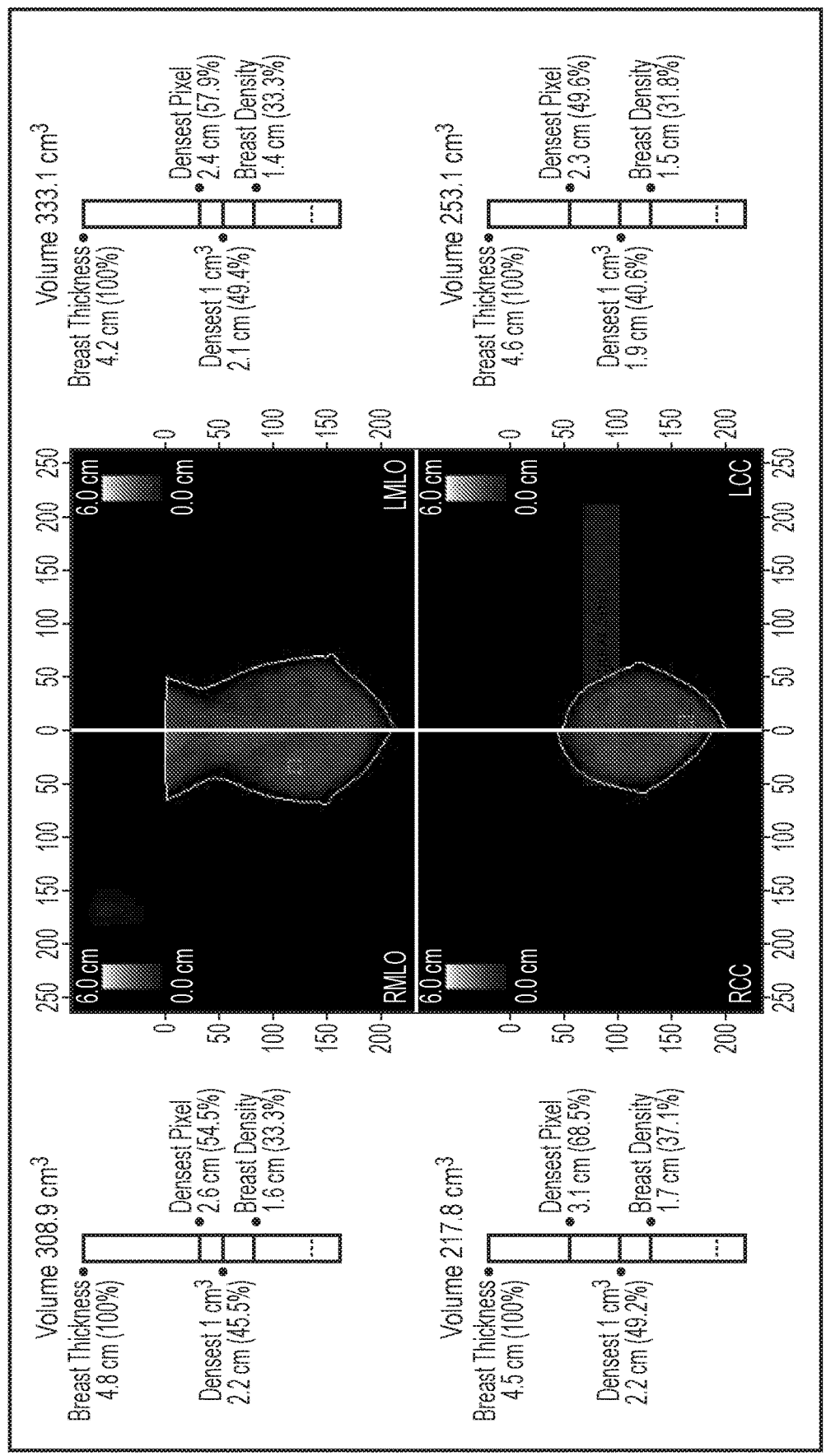
FIG. 4 shows a standardised display comprising right and left MLO images, right and left CC images, volume of the portion of the breast in each view, breast thickness, breast density, densest centimetre and densest pixel.
Figure 5A:
FIG. 5(a) illustrates a typical presentation of a digital mammogram.
Figure 5B:
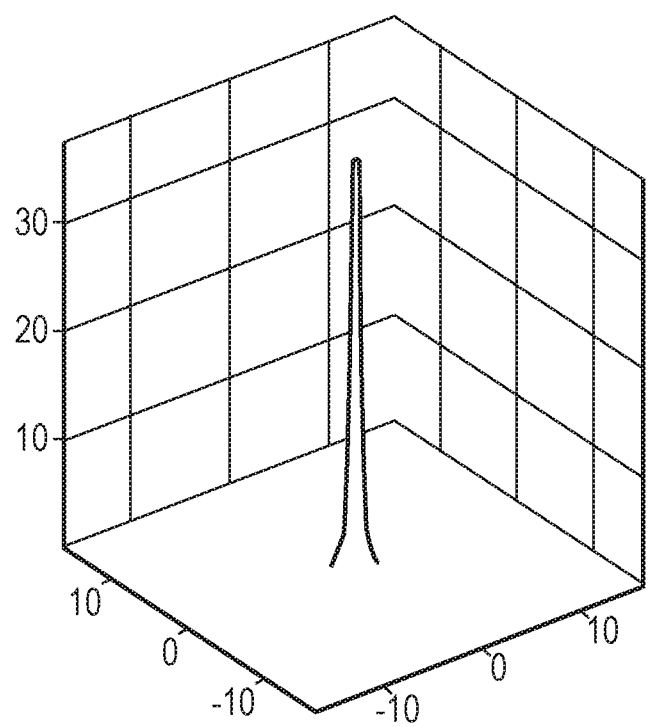
FIG. 5(b) shows the mammogram 2D eNPS after 0th order polynomial detrending.
Figure 5C:
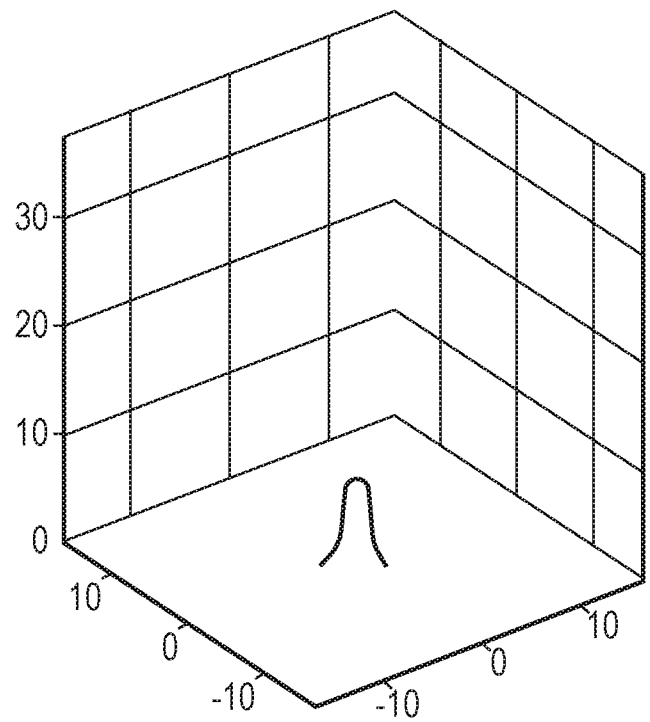
FIG. 5(c) shows the mammogram 2D eNPS after 2nd order polynomial detrending.
Figure 5D:
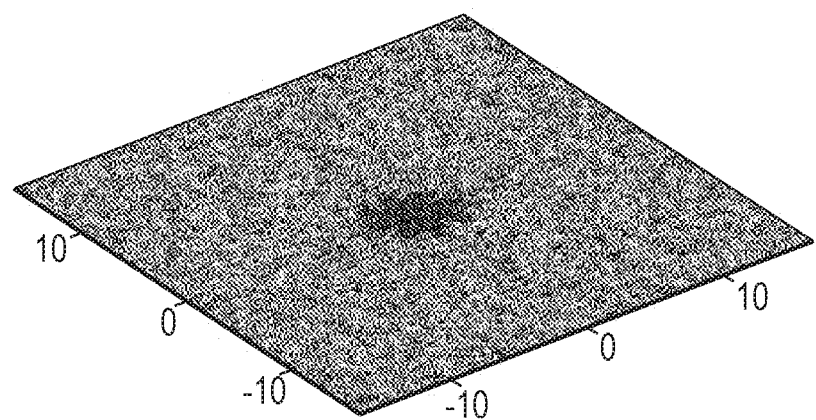
FIG. 5(d) is a plot of the mammogram 2D eNPS after data was removed at spatial frequencies with a significant difference between the eNPS in (b) and (c) (i.e., "hole" in centre)
Figure 5E:
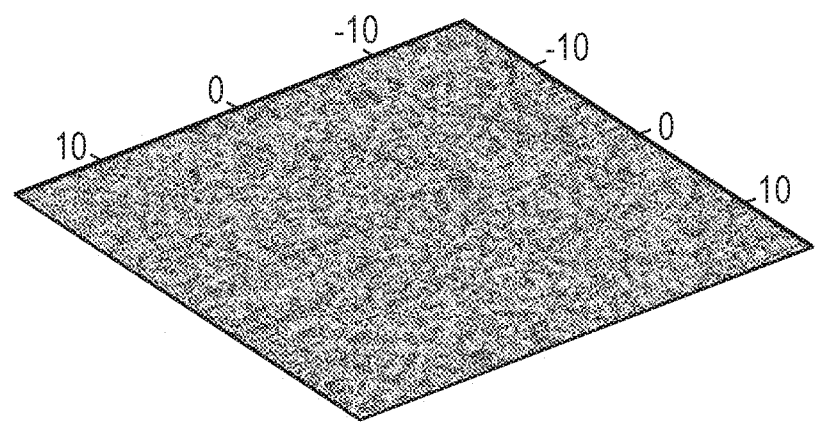
FIG. 5(e) illustrates the resulting estimate of the mammogram NPS after interpolation of data in (d)

In one embodiment related to FIG. 3, the images are received on a tablet device (i.e. due to time restraints) for review before the clinician 'accepts' the image. In further embodiments the result of the per-image quality assessment is transmitted back to a scanner console; sent to a mobile communications application; or other means such as an audible, for example, a vocal signal.

It is an advantage of the system, in one embodiment, that all images, including rejected images, are captured and stored and the data becomes integral to a counter data statistical model that will further provide means for machine learning enhancement of the solution.

Further advantages of the present invention relate to automatic means to extend image data analysis in the Cloud; and to the automatic removal and re-application of protected health information to anonymized data in the Cloud.

By way of illustrative example, the present invention provides improved means to combine various data points for breast imaging centres to get to 'Overall Quality' and 'Overall Effectiveness' scores where:

Overall Quality=(% AverageDoseOverExpected)
*k1+(% AveragePressureOverExpected)*k2+(% AverageQualityOverExpected)*k3+(CancerDetectionRate)*k4+(RecallRate)*k5+(Sensitivity)*k6+(Specificity)*k7+(IntervalCancerRate)*k8+(InvasiveCancerRate)*k9+(MinimalSignsRate)*k10+ . . . .

OverallEffectiveness=(% Capacity)*k11+(% ReturningPatientRate)*k12+(% EquipmentUtilizationRate)*k13+(% EquipmentUptimeRate)*k14+(DelayBeforeDx)*k15+(DelayBeforeBx)*k16+(DelayBeforePathology)*k17+(DelayBeforeTreatment)*k16+ . . . .

The factors k1 to k16 are determined from optimization on a training data set.

The Overall Quality score can be shown versus Overall Productivity score to demonstrate Overall Effectiveness, for example, the effectiveness of a breast imaging centre. And then those numbers compared between sites within an organisation to ascertain which centre or centres is optimizing productivity without compromising quality. The scores can also be compared to unaffiliated institutions, or regional, state or national metrics to see how one Enterprise compares to another.

Additionally, the Overall Effectiveness and Overall Productivity can be mapped or otherwise displayed for example plotted in a form such as that shown in FIG. 1.

If the imaging data is received from different imaging apparatus and modalities between imaging centres, the data is standardized, for example, a standard radiation dose measurement algorithm might be applied. Similarly, a standardized compression measurement applied which might, for example, prioritise pressure in preference to force. Obtained cancer detection rate and other clinical parameters might be achieved via integration and data collection from other electronic systems.

Many breast imaging centres do not store raw data from mammograms on the premises. If a new algorithm becomes available that provides significant new data with important meaning if evaluated temporally, a process can be executed that will retrieve raw data from historic cases from the Cloud back to the facility, re-identify it, re-process it, then send the new results on the historic data to the Cloud. In that manner, temporal comparison becomes available shortly after deployment of a new algorithm.

The invention has been described by way of examples only. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the claims.

The invention claimed is:

1. A method for providing a quantitative assessment of an image including the steps of:
using an imaging apparatus to obtain at least one breast x-ray image of a patient;
determining a linearized image intensity from the breast x-ray image;
obtaining image data from the breast x-ray image;
deriving a breast x-ray image parameter from the image data;
determining a two-dimensional effective noise power spectrum (eNPS) using subtraction of a two-dimensional second or higher order fit from the linearized image intensity;
obtaining from the image data a metric including amount of image sharpness for assessment with the image parameter and eNPS; and
identifying location(s) on the breast x-ray image where the amount of image sharpness is below a level by determining the eNPS magnitude within a spatial frequency range, and providing an indication of the location(s) on the breast x-ray image where the amount of image sharpness is below the level.

2. The method of claim 1 wherein the image parameter is derived for a region of the breast x-ray image.

3. The method of claim 1 including accounting in the image power spectra for influence by noise from the apparatus.

4. The method of claim 1 including statistically accounting in the image power spectra for influence by noise from an anatomical structures in a soft tissue in the breast x-ray image.

5. The method of claim 1 including the step of determining whether the sharpness of an image below the preselected level is attributable to motion of the soft tissue while obtaining the image.

6. The method of claim 1 including determining the sharpness below the preselected level in or proximate an anatomical artefact in a breast of the patient.

7. The method of claim 6 including determining the sharpness below the preselected level attributable to motion of the anatomical artefact in soft tissue in the breast x-ray image while obtaining the image.

8. The method of claim 1 including determining the density of tissue in the breast as the image parameter and identifying where there is overlap of the location(s) where the sharpness is below the preselected level and location(s) where the density is above a preselected criteria.

9. The method of claim 1 wherein the image parameter derived includes thickness, composition, or density of a compressed breast included in soft tissue in the breast x-ray image.

10. The method of claim 8 including determining whether regions of interest (ROI) within a constant thickness region within the tissue overlap on the image.

11. The method of claim 1 wherein the contrast relating to the statistical data is computed from the image intensity of pixels at locations where the density is relatively high and low.

12. The method of claim 1 wherein the imaging quality metrics include positioning metrics derived from the location and orientation of the soft tissue in the breast x-ray image.

13. The method of claim 1 including characterising the breast x-ray image by scores derived the data, parameter(s), and metric(s).

14. The method of claim 13 including classifying the scores according to information of the imaging apparatus, clinic where the image is acquired, or clinician who obtained the images.

15. The method of claim 13 including deriving an Overall Quality score from a plurality of the scores.

16. The method of claim 13 including deriving an Overall Productivity score from a plurality of the scores.

17. The method of claim 16 including deriving an overall Effectiveness score, an overall Quality score and an overall productivity score.

18. The method of claim 1 including:
reading a compression force recorded while obtaining the breast x-ray image;
analyzing the image and deriving a target force for applying a target compression pressure to be applied to soft tissue of the patient by the apparatus for obtaining a next image; and
including the target force in a feedback delivered to a user.

19. A system for providing a quantitative assessment of an image for implementing the method of claim 1.

* * * * *